US009215987B2

(12) United States Patent
Trayanova et al.

(10) Patent No.: US 9,215,987 B2
(45) Date of Patent: Dec. 22, 2015

(54) METHODOLOGY FOR ARRHYTHMIA RISK STRATIFICATION BY ASSESSING QT INTERVAL INSTABILITY

(75) Inventors: Natalia A. Trayanova, Baltimore, MD (US); Xiaozhong Chen, Hoover, AL (US)

(73) Assignee: The Johns Hopkins University, Baltimore, MD (US)

( * ) Notice: Subject to any disclaimer, the term of this patent is extended or adjusted under 35 U.S.C. 154(b) by 745 days.

(21) Appl. No.: 13/515,477

(22) PCT Filed: Dec. 16, 2010

(86) PCT No.: PCT/US2010/060843
§ 371 (c)(1),
(2), (4) Date: Jun. 12, 2012

(87) PCT Pub. No.: WO2011/084636
PCT Pub. Date: Jul. 14, 2011

(65) Prior Publication Data
US 2013/0102912 A1    Apr. 25, 2013

Related U.S. Application Data

(60) Provisional application No. 61/286,986, filed on Dec. 16, 2009.

(51) Int. Cl.
| | | |
|---|---|---|
| A61B 5/04 | (2006.01) | |
| A61B 5/0468 | (2006.01) | |
| A61B 5/0402 | (2006.01) | |
| A61B 5/0464 | (2006.01) | |
| A61B 5/00 | (2006.01) | |

(52) U.S. Cl.
CPC ......... *A61B 5/04017* (2013.01); *A61B 5/04028* (2013.01); *A61B 5/0464* (2013.01); *A61B 5/0468* (2013.01); *A61B 5/7275* (2013.01)

(58) Field of Classification Search
None
See application file for complete search history.

(56) References Cited

U.S. PATENT DOCUMENTS

| | | |
|---|---|---|
| 2002/0188214 A1 | 12/2002 | Misczynski et al. |
| 2003/0130586 A1* | 7/2003 | Starobin et al. ............... 600/515 |
| 2005/0004486 A1 | 1/2005 | Glass et al. |

(Continued)

OTHER PUBLICATIONS

Akar et al., Transmural electrophysiological heterogeneities underlying arrhythmogenesis in heart failure. Circ Res. 2003;93(7):638-645.

(Continued)

*Primary Examiner* — Brian T Gedeon
(74) *Attorney, Agent, or Firm* — Venable LLP; Henry J. Daley

(57) ABSTRACT

A method of predicting ventricular arrhythmias includes receiving an electrical signal from a subject's heart for a plurality of heart beats, identifying characteristic intervals and heart beat durations of the electrical signal corresponding to each of the plurality of heart beats to provide a plurality of characteristic intervals with corresponding heart beat durations, representing dynamics of the plurality of characteristic intervals as a function of a plurality of preceding characteristic intervals and durations of corresponding heart beats over a chosen period time, assessing a stability of the function over the chosen period of time, and predicting ventricular arrhythmias based on detected instabilities in the dynamics of the characteristic intervals.

23 Claims, 13 Drawing Sheets

(56) References Cited

U.S. PATENT DOCUMENTS

2006/0074332 A1 4/2006 Bischoff et al.
2009/0048527 A1 2/2009 Hatib et al.

OTHER PUBLICATIONS

Akar et al., Unique topographical distribution of M cells underlies reentrant mechanism of torsade de pointes in the long-QT syndrome. *Circulation.* 2002; 105(10): 1247-1253.
Akhbardeh et al., A Modified Blind Segmentation Method for Ballistocardiogram Cycle Extraction. *EA4BC 2007, 29th Annual International Conference of the IEEE Engineering in Medicine and Biology Society, Lyon, France.* 2007.
Akhbardeh et al., Towards the Experimental Evaluation of Novel Supervised Fuzzy Adaptive Resonance Theory for Pattern Classification. *Pattern Recognition Letters.* 2007;29(8): 1082-1093.
Akhbardeh, Signal Classification using Novel Pattern Recognition Methods and Wavelet Transforms. *PhD Thesis, Tampere University of Technology, Finland* 2007.
Arevalo et al., Arrhythmogenesis in the heart. Multiscale modeling of the effects of defibrillation shocks and the role of electrophysiological heterogeneity. *Chaos.* 2007;17(1) : 015103.
Ashihara et al., Tunnel propagation of postshock activations as a hypothesis for fibrillation induction and isoelectric window. *Circ Res.* 2008;102(6):737-745.
Banville et al., Effect of action potential duration and conduction velocity restitution and their spatial dispersion on alternans and the stability of arrhythmias. *J Cardiovasc Electrophysiol.* 2002:13(11) : 1141-1149.
Berger et al., Beat-to-beat QT interval variability: novel evidence for repolarization lability in ischemic and nonis chemic dilated card iomyop athy. Circulation. 1997;96(5):1557-1565.
Bonnemeier et al., Impact of infarct-related artery flow on QT dynamicity in patients undergoing direct percutaneous coronary intervention for acute myocardial infarction. Circulation. 2003;108(24):2979-2986.
Bonnemeier et al., Temporal repolarization inhomogeneity and reperfusion arrhythmias in patients undergoing successful primary percutaneous coronary intervention for acute ST-segment elevation myocardial infarction: Impact of admission troponin T. *Am Heart J.* 2003;145(3):484-492.
Brunie et al., A Fast Version of the Schur Cohn Algorithm. *J. of Complexity, 2000;16:54-69.*
Cao et al., Spatiotemporal heterogeneity in the induction of ventricular fibrillation by rapid pacing: importance of cardiac restitution properties. *Circ Res.* 1999 ; 84(11) :1318-1331.
Chen et al., Novel QT Stability Monitoring Algorithm in Clinical ECG Recordings. *Heart Rhythm.* 2009;6(No. 5 May Supplement): S332.
Chen et al., Head-tail interactions in numerical simulations of reentry in a ring of cardiac tissue. *Heart Rhythm.* 2005;2(9):1038-1046.
Chevalier et al., dynamicity and sudden death after myocardial infarction: results of a long-term follow-up study. J Cardiovasc Electrophysiol. 2003;14(3):227-233.
Chinushi et al., Electrophysiological basis of arrhythmogenicity of QT/T alternans in the long-QT syndrome: tridimensional analysis of the kinetics of cardiac repolarization. Circ Res. 1998;83(6):614-628.
Company-Bosch E, Hartmann E. ECG Front-End Design is simplified with MicroConverter. http://;www.analog.com/libraty'analo .Dialogue/archives/37-11 %ecg.litrni.
Drouin et al., Electrophysiologic characteristics of cells spanning the left ventricular wall of human heart: evidence for presence of M cells. *J Am Coll Cardiol.* 1995;26(1):185-192.
Elharrar et al., Cycle length effect on restitution of action potential duration in dog cardiac fibers. *Am J Physiol.* 1983;244(6):H782-792.
Fenton et al., Memory in an Excitable Medium: A Mechanism for Spiral Wave Breakup in the Low-Excitability Limit. *Phys. Rev. Lett.* 1999;83(19):3964-3967.
Fossa et al., Analyses of Dynamic Beat-to-Beat QT-TQ Interval (ECG Restitution) Changes in Humans under Normal Sinus Rhythm and Prior to an Event of Torsades de Pointes during QT Prolongation Caused by Sotalol. *Ann Noninvasive Electrocardiol.* 2007;12(4):338-348.
Franz et al., Cycle length dependence of human action potential duration in vivo. Effects of single extrastimuli, sudden sustained rate acceleration and deceleration, and different steady-state frequencies. *J Clin Invest.* 1988;82(3):972-979.
Gajic, Linear Dynamics Systems and Signals. *Prentice Hall* 2003.
Garfinkel et al., Preventing ventricular fibrillation by flattening cardiac restitution. *PNAS.* 2000;97(11).
Gilmour et al., Electrical Restitution, Critical Mass, and the Riddle of Fibrillation. *J. Cardiovasc Electrophysiol.* 1999 ;10(8) : 1087-1089.
Gilmour et al., Memory and complex dynamics in cardiac Purkinje fibers. *American Journal of Physiology.* 1997;272(4):H1826.
Gilmour et al., Time-and rate-dependent alterations of the QT interval precede the onset of torsade de pointes in patients with acquired QT prolongation. *JACC.* 1997;30:209-217.
Gima et al., Ionic current basis of electrocardiographic waveforms: a model study. *Circ Res.* 2002;90(8): 889-896.
Huang et al., Restitution properties during ventricular fibrillation in the in situ swine heart. *Circulation.* 2004;110(20):3161-3167.
Huikuri et al., Frequency domain measures of heart rate variability before the onset of nonsustained and sustained ventricular tachycardia in patients with coronary artery disease. *Circulation.* 1993 ;87(4): 1220-1228.
Jain et al., Correlation between dispersion of repolarization (QT dispersion) and ventricular ectopic beat frequency in patients with acute myocardial infarction: a marker for risk of arrhythmogenesis? *International Journal of Cardiology.* 2004;93(1):69-73.
Karagueuzian et al., Action potential alternans and irregular dynamics in quinidine-intoxicated ventricular muscle cells. Implications for ventricular proarrhythmia. *Circulation.* 1993;87(5):1661-1672.
Kepski et al., Adaptive Filtering in Exercise High Resolution ECG as Applied to the Hypertrophic Cardiomyopathy. *Journal of Pacing and Clinical Electrophysiology.* 2001;24(8).
Kleiger et al., Decreased heart rate variability and its association with increased mortality after acute myocardial infarction. *Am J Cardiol.* 1987;59(4):256-262.
Lathi BP. Linear Systems and Signals. *Berkeley-Cambridge Press.* 1992:227.
Laurita et al., Modulation of ventricular repolarization by a premature stimulus. Role of epicardial dispersion of repolarization kinetics demonstrated by optical mapping of the intact guinea pig heart. Circ Res. 1996;79(3):493-503.
Li et al., Ion channel basis for alternans and memory in cardiac myocytes. *Ann Biomed Eng.* 2003;31(10):1213-1230.
Li et al., Myocardial ischemia lowers precordial thump efficacy: an inquiry into mechanisms using three-dimensional simulations. *Heart Rhythm.* 2006;3(2): 179-186.
Maharaj et al., The role of transmural ventricular heterogeneities in cardiac vulnerability to electric shocks. *Frog Biophys Mol Biol.* 2008;96(1-3):321-338.
Merri et al., Relation between ventricular repolarization duration and cardiac cycle length during 24-hour Holier recordings. Findings in normal patients and patients with long QT syndrome. Circulation. 1992;85(5):1816-1821.
Murabayashi et al., Beat-to-beat QT interval variability associated with acute myocardial ischemia. *J Electrocardiol.* 2002;35(1):19-25.
Nash et al., Whole heart action potential duration restitution properties in cardiac patients: a combined clinical and modelling study. *Experimental Physiology.* 2006;91:339-354.
Nolasco et al., A graphic method for the study of alternation in cardiac action potentials. *J Appl Physiol.* 1968;25(2) : 191-196.
Osaka et al., Changes in autonomic activity preceding onset of nonsustained ventricular tachycardia. *Ann Noninvasive Electrocardiol.* 1996;1(1):3-11.
Otani et al., Memory Models for the Electrical Properties of Local Cardiac Systems. J. Theor. Biol. 1997;187:409-436.
Park et al., Application of a wavelet adaptive filter to minimize distortion of the T-segment. *Med Biol. Eng. Comput.* 1998;36:581-586.

(56) References Cited

OTHER PUBLICATIONS

Pitruzzello et al., Spatial heterogeneity of the restitution portrait in rabbit epicardium. *Am J Physiol Heart Circ Physiol.* 2007;292:H1568-H1578.

Plank et al., From mitochondrial ion channels to arrhythrmas in the heart: computational techniques to bridge the spatio-temporal scales. *Phil. Trans. R. Soc. A.* 2008;366:3381-3409.

Pressl et al., Automatically Generated, Anatomically Accurate Meshes for Cardiac Electrophysiology problems. *IEEE-TBME.* 2009;56:1318-1330.

Qu et al., Mechanisms of discordant alternans and induction of reentry in simulated cardiac tissue. *Circulation.* 2000;102(14):1664-1670.

Renumadhavi et al., A new approach for evaluating SNR of ECG signals and its implementation. *Proceedings of the 6th WSEAS International Conference on Simulation, Modelling and Optimization, Lisbon, Portugal.* 2006:202-205.

Riccio et al., Electrical restitution and spatiotemporal organization during ventricular fibrillation. *Circ Res.* 1999;84(955-963).

Rodriguez et al., Differences between left and right ventricular chamber geometry affect cardiac vulnerability to electric shocks. *Circ Res.* 2005;97(2):168-175.

Rodriguez et al., Cardiac vulnerability to electric shocks during phase 1A of acute global ischemia. *Heart Rhythm.* 2004;1(6):695703.

Rodriguez et al., Modeling cardiac ischemia. *Ann N Y Acad Sci.* 2006;1080:395-414.

Saitoh et al., Action potential duration alternans in dog Purkinje and ventricular muscle fibers. Further evidence in support of two different mechanisms. *Circulation.* 1989;80(5):1421-1431.

Sampson et al., Simulation and prediction of functional block in the presence of structural and ionic heterogeneity. *Am J Physiol Heart Circ Physiol.* 2001;281(6): H2597-2603.

Schwartz et al., QT interval prolongation as predictor of sudden death in patients with myocardial infarction. *Circulation.* 1978;57(6):1074-1077.

Shusterman et al., Autonomic nervous system activity and the spontaneous initiation of ventricular tachycardia. ESVEM Investigators. Electrophysiologic Study Versus Electrocardiographic Monitoring Trial. *J Am Coll Cardiol.* 1998;32(7):1891-1899.

Szydlo et al., QT/RR relationship in patients after remote anterior myocardial infarction with left ventricular dysfunction and different types of ventricular arrhythmias. Ann Noninvasive Elecirocardiot 2008;13(1): 61-66.

Ten Tusscher et al., A model for human ventricular tissue. *Am JPhysiol Heart Circ Physiol.* 2004;286(4): H1573-1589.

Ten Tusscher et al., Alternans and spiral breakup in a human ventricular tissue model. *Am JPhysiol Heart Circ Physiol* 2006;291:H1088-H1100.

Tereshchenko et al., Prediction of Ventricular Tachyarrhythmias by Intracardiac Repolarization Variability Analysis. *Circulation: Arrhythmia and Electrophysiology.* 2009;2:276-284.

Thakor et al., Applications of Adaptive Filtering to ECG Analysis: Noise Cancellation and Arrhythmia Detection. *IEEE Transactions on Biomedical Engineering.* 1991;18(8).

Tice et al., Mechanistic investigation into the arrhythmogenic role of transmural heterogeneities in regional ischaemia phase 1A. *Europace.* 2007;9 Suppl 6•vi46-58.

Trayanova et al., Computer simulations of cardiac defibrillation: a look inside the heart. *Computing and Visualization in Science.* 2002;4(4):259-270.

Vadakkumpadan et al., Image-Based Models of Cardiac Structure in Health and Disease. *Wiley Interdisciplinary Reviews: Systems Biology and Medicine.* 2009(In press).

Vadakkumpadan et al., Image-based models of cardiac structure with applications in arrhythmia and defibrillation studies. *J. Electrocardiology.* 2009;42: 157. e 15 1-157. el10.

Vigmond et al., Towards predictive modelling of the electrophysiology of the heart. *Exp. Physiol.* 2009;94(5):563-577.

Vigmond et al., The Role of Vagal Stimulation on Atrial Arrhythmogenesis. Proceedings of the Second Joint EMBS/BMES Confereence. 2002.

Vrtovee et al., Beat-to-beat QT interval variability in coronary patients. *J Electrocardiol.* 2000; 33(2):119-125.

Weiss et al., Electrical restitution and cardiac fibrillation. *J Cardiovasc Electrophysiol.* 2002; 13(3):292-295.

Yamauchi et al., Restitution properties and occurrence of ventricular arrhythmia in LQT2 type of long QT syndrome. *J Cardiovasc Electrophysiol.* 2002;13(9) : 910-9 14.

Yan et al., Characteristics and distribution of M cells in arterially perfused canine left ventricular wedge preparations. *Circulation.* 1998;98(18): 1921-1927.

Huang, et al., Restitution Properies During Ventricular Fibrillation in the In Situ Swine Heat, Circulation, Journal of the American Heart Association, 2004, 110:316-3167.

International Search Report and Written Opinion of PCT/US2010/060843.

* cited by examiner

METHODOLOGY FOR ARRHYTHMIA RISK STRATIFICATION BY ASSESSING QT INTERVAL INSTABILITY

CROSS-REFERENCE OF RELATED APPLICATION

This application claims priority to U.S. Provisional Application No. 61/286,986 filed Dec. 16, 2009, the entire contents of which are hereby incorporated by reference, and is a national stage application under 35 U.S.C. §371 of PCT/US2010/060843 filed Dec. 16, 2010, the entire contents of which are incorporated herein by reference.

This invention was made with Government support of Grant No. HL082729, awarded by the Department of Health and Human Service, The National Institutes of Health (NIH). The U.S. Government has certain rights in this invention.

BACKGROUND

1. Field of Invention

The field of the currently claimed embodiments of this invention relates to systems and methods of predicting risk of ventricular arrhythmias.

2. Discussion of Related Art

Sudden cardiac death (SCD) is a major health problem in the industrialized world. SCD often occurs in healthy individuals without prior history of heart disease. The early diagnosis of arrhythmia has the potential to significantly reduce mortality due to SCD. Clinical studies have demonstrated that instability in the QT interval of the electrocardiogram (ECG), which is the global manifestation of instability in ventricular repolarization, predicts propensity to arrhythmias. However, a robust methodology to assess QT interval instability and thus predict propensity to arrhythmia in a patient-specific manner is currently lacking.

Clinical studies have demonstrated that the QT interval instability in the ECG signal is associated with a propensity for lethal arrhythmias. A methodology that allows the physician to predict the development of instabilities in the QT interval in a patient-specific manner, and thus predict the patient's propensity for arrhythmias, would be a significant step forward in improving SCD risk stratification and in preventing loss of human life.

ECG (or electrogram if recorded from an implanted cardioverter-defibrillator (ICD) device) is the most widely-used tool in the diagnosis of heart rhythm disorders. The QT interval of the ECG (interval between Q and T deflections, FIG. 1A) has been found to be unstable in the diseased heart (FIG. 1B). QT interval instability has been reported in long QT syndrome patients (Merri M, Moss A J, Benhorin J, Locati E H, Alberti M, Badilini F. Relation between ventricular repolarization duration and cardiac cycle length during 24-hour Holter recordings. Findings in normal patients and patients with long QT syndrome. *Circulation*. 1992; 85(5):1816-1821; Yamauchi S, Yamaki M, Watanabe T, Yuuki K, Kubota I, Tomoike H. Restitution properties and occurrence of ventricular arrhythmia in LQT2 type of long QT syndrome. *J Cardiovasc Electrophysiol.* 2002; 13(9):910-914; Chinushi M, Restivo M, Caref E B, El-Sherif N. Electrophysiological basis of arrhythmogenicity of QT/T alternans in the long-QT syndrome: tridimensional analysis of the kinetics of cardiac repolarization. *Circ Res.* 1998; 83(6):614-628). QT prolongation and abnormal QT dynamics have been found in acute myocardial infarction patients (Chevalier P, Burri H, Adeleine P, Kirkorian G, Lopez M, Leizorovicz A, Andre-Fouet X, Chapon P, Rubel P, Touboul P. QT dynamicity and sudden death after myocardial infarction: results of a long-term follow-up study. *J Cardiovasc Electrophysiol.* 2003; 14(3):227-233; Schwartz P J, Wolf S. QT interval prolongation as predictor of sudden death in patients with myocardial infarction. *Circulation*. 1978; 57(6):1074-1077; Bonnemeier H, Wiegand U K, Bode F, Hartmann F, Kurowski V, Katus H A, Richardt G. Impact of infarct-related artery flow on QT dynamicity in patients undergoing direct percutaneous coronary intervention for acute myocardial infarction. *Circulation*. 2003; 108(24):2979-2986; Szydlo K, Trusz-Gluza M, Wita K, Filipecki A, Orszulak W, Urbanczyk D, Krauze J, Kolasa J, Tabor Z. QT/RR relationship in patients after remote anterior myocardial infarction with left ventricular dysfunction and different types of ventricular arrhythmias. *Ann Noninvasive Electrocardiol.* 2008; 13(1):61-66). Berger et al. reported an increased QT interval variability in dilated cardiomyopathy patients (FIG. 1B) (Berger R D, Kasper E K, Baughman K L, Marban E, Calkins H, Tomaselli G F. Beat-to-beat QT interval variability: novel evidence for repolarization lability in ischemic and nonischemic dilated cardiomyopathy. *Circulation*. 1997; 96(5):1557-1565). These studies indicate that the instability in the QT interval is an important indicator of cardiac rhythm disorder.

Instability in the QT interval is a manifestation of instability in repolarization in the heart. At the cellular level, instability in myocyte repolarization is assessed from the dynamics of its action potential duration (APD). APD instability and its implication for arrhythmogenesis have been extensively studied (Laurita K R, Girouard S D, Rosenbaum D S. Modulation of ventricular repolarization by a premature stimulus. Role of epicardial dispersion of repolarization kinetics demonstrated by optical mapping of the intact guinea pig heart. *Circ Res.* 1996; 79(3):493-503; Akar F G, Rosenbaum D S. Transmural electrophysiological heterogeneities underlying arrhythmogenesis in heart failure. *Circ Res.* 2003; 93(7):638-645; Sampson K J, Henriquez C S. Simulation and prediction of functional block in the presence of structural and ionic heterogeneity. *Am J Physiol* 2001; 281(6):H2597-2603; Chen X, Fenton F H, Gray R A. Head-tail interactions in numerical simulations of reentry in a ring of cardiac tissue. *Heart Rhythm.* 2005; 2(9):1038-1046; Weiss J N, Chen P S, Qu Z, Karagueuzian H S, Lin S F, Garfinkel A. Electrical restitution and cardiac fibrillation. *J Cardiovasc Electrophysiol.* 2002; 13(3):292-295; Gilmour R F, Chialvo D R. Electrical Restitution, Critical Mass, and the Riddle of Fibrillation. *J. Cardiovasc Electrophysiol.* 1999; 10(8):1087-1089; Banville I, Gray R A. Effect of action potential duration and conduction velocity restitution and their spatial dispersion on alternans and the stability of arrhythmias. *J Cardiovasc Electrophysiol.* 2002; 13(11):1141-1149; Elharrar V, Surawicz B. Cycle length effect on restitution of action potential duration in dog cardiac fibers. *Am. J. Physiol.* 1983; 244(6):H782-792; Gilmour R F, Otani N F, Watanabe M A. Memory and complex dynamics in cardiac Purkinje fibers. *Am J. Physiol.* 1997; 272(4):H1826; Franz M R, Swerdlow C D, Liem L B, Schaefer J. Cycle length dependence of human action potential duration in vivo. Effects of single extrastimuli, sudden sustained rate acceleration and deceleration, and different steady-state frequencies. *J Clin Invest.* 1988; 82(3):972-979). It is thus reasonable to expect that concepts developed to determine instability in APD could be translated to the clinic and applied in the evaluation of the patient's QT interval instability. The efforts to assess instability in APD are therefore reviewed below.

APD depends on the preceding diastolic interval (DI). This relationship is termed APD restitution. A standard APD restitution curve is constructed by delivering S2 pacing stimuli following the same S1 pacing train for a broad range of S1-S2 intervals; S1 pacing is at a constant rate. In a dynamic APD restitution protocol, tissue is paced continuously at different rates; the last beat for each pacing episode is used to construct the APD restitution. The restitution hypothesis postulates that APD can be predicted from the preceding DI and the restitution relationship (FIG. 2), and implicates the maximum slope of the APD restitution curve as the sole predictor of repolarization instability and thus of propensity to arrhythmia (Nolasco J B, Dahlen R W. A graphic method for the study of alternation in cardiac action potentials. *J Appl Physiol*. 1968; 25(2):191-196; Garfinkel A, Kim Y H, Voroshilovsky O, Qu Z, Kil. Preventing ventricular fibrillation by flattening cardiac restitution. *PNAS*. 2000; 97(11); Riccio M L, Koller M L, Gilmour R F. Electrical restitution and spatiotemporal organization during ventricular fibrillation. *Circ Res*. 1999; 84:955-963). Indeed, studies have shown that steep restitution increases the functional heterogeneity of repolarization (Garfinkel A, Kim Y H, Voroshilovsky O, Qu Z, Kil. Preventing ventricular fibrillation by flattening cardiac restitution, *PNAS*, 2000; 97(11); Riccio M L, Koller M L, Gilmour R F. Electrical restitution and spatiotemporal organization during ventricular fibrillation. *Circ Res*, 1999; 84(955-963); Qu Z, Garfinkel A, Chen P S, Weiss J N. Mechanisms of discordant alternans and induction of reentry in simulated cardiac tissue. *Circulation*. 2000; 102(14):1664-1670; Cao J M, Qu Z, Kim Y H, Wu T J, Garfinkel A, Weiss J N, Karagueuzian H S, Chen P S. Spatiotemporal heterogeneity in the induction of ventricular fibrillation by rapid pacing: importance of cardiac restitution properties. *Circ Res*. 1999; 84(11):1318-1331), and leads to arrhythmogenesis (Akar F G, Rosenbaum D S. Transmural electrophysiological heterogeneities underlying arrhythmogenesis in heart failure. *Circ Res*. 2003; 93(7):638-645; Chen X, Fenton F H, Gray R A. Head-tail interactions in numerical simulations of reentry in a ring of cardiac tissue. *Heart Rhythm* 2005; 2(9):1038-1046). Studies have also reported that a steep restitution causes APD alternans at the cellular level (Nolasco J B, Dahlen R W. A graphic method for the study of alternation in cardiac action potentials. *J Applied Physiol*. 1968; 25(2):191-196) and results in spiral wave breakup and the induction of ventricular fibrillation (VF) (Weiss J N, Chen P S, Qu Z, Karagueuzian H S, Lin S F, Garfinkel A. Electrical restitution and cardiac fibrillation. *J Cardiovasc Electrophysiol*. 2002; 13(3):292-295; Gilmour R F, Chialvo DR. Electrical Restitution, Critical Mass, and the Riddle of Fibrillation. *J. Cardiovasc Electrophysiol*. 1999; 10(8):1087-1089).

The assessment of APD stability, and thus the prediction of propensity to arrhythmia based on the criterion of maximum restitution slope >1 is, however, not always accurate: arrhythmia has been induced with slope <1, and failed to be induced with slope >1 (Elharrar V, Surawicz B. Cycle length effect on restitution of action potential duration in dog cardiac fibers. *Am J. Physiol*. 1983; 244(6):H782-792; Gilmour R F, Otani N F, Watanabe M A. Memory and complex dynamics in cardiac Purkinje fibers. *Am J. Physiol*. 1997; 272(4):H1826; Franz M R, Swerdlow C D, Liem L B, Schaefer J. Cycle length dependence of human action potential duration in vivo. Effects of single extrastimuli, sudden sustained rate acceleration and deceleration, and different steady-state frequencies. *J Clin Invest*. 1988; 82(3):972-979; Saitoh H, Bailey J C, Surawicz B. Action potential duration alternans in dog Purkinje and ventricular muscle fibers. Further evidence in support of two different mechanisms. *Circulation*. 1989; 80(5):1421-1431; Karagueuzian H S, Khan S S, Hong K, Kobayashi Y, Denton T, Mandel W J, Diamond G A. Action potential alternans and irregular dynamics in quinidine-intoxicated ventricular muscle cells. Implications for ventricular proarrhythmia. *Circulation*. 1993; 87(5):1661-1672). Huang et al., evaluating the effect of previous activations on APD with a statistical approach (Huang J, Zhou X, Smith W M, Ideker R E. Restitution properties during ventricular fibrillation in the in situ swine heart. *Circulation*. 2004; 110(20):3161-3167), reported that during VF, the contribution of preceding APD to current APD is as significant as the contribution of the preceding DI. These results indicate that events that precede DI also affect stability of APD.

The events that precede DI represent the activation history, i.e. memory (FIG. 3). Memory has been found to affect APD and its restitution. Elharrar et al (Elharrar V, Surawicz B. Cycle length effect on restitution of action potential duration in dog cardiac fibers. *Am J. Physiol*. 1983; 244(6):H782-792) reported that APD restitution depended on pacing rate. Gilmour and Otani (Otani N F, Gilmour R F. Memory Models for the Electrical Properties of Local Cardiac Systems. *J. Theor. Biol*. 1997; 187:409-436) found that that memory can enhance or diminish APD stability. These studies indicate that both restitution and memory govern APD stability.

Similar to instability in APD, the restitution concept has been used to evaluate QT interval instability in the clinic by evaluating the slope of the dependence of the QT interval on the preceding TQ interval or preceding RR interval (since QT interval+QT interval is equal to RR interval) (FIG. 1A). The latter relationship has been tested as an arrhythmia risk predictor (Yamauchi S, Yamaki M, Watanabe T, Yuuki K, Kubota I, Tomoike H. Restitution properties and occurrence of ventricular arrhythmia in LQT2 type of long QT syndrome. *J Cardiovasc Electrophysiol*. 2002; 13(9):910-914; Fossa A A, Wisialowski T, Crimin K, Wolfgang E, Couderc J-P, Hinterseer M, Kaab S, Zareba W, Badilini F, Sarapa N. Analyses of Dynamic Beat-to-Beat QT-TQ Interval (ECG Restitution) Changes in Humans under Normal Sinus Rhythm and Prior to an Event of Torsades de Pointes during QT Prolongation Caused by Sotalol. *Ann Noninvasive Electrocardiol*. 2007; 12(4):338-348; Gilmour R F, Riccio M L, Locati E H, Maison-Blanche P, Coumel P, Schwartz P J. Time- and rate-dependent alterations of the QT interval precede the onset of torsade de pointes in patients with acquired QT prolongation. *J Am Coll Cardiol*. 1997; 30:209-217). However, such an approach is invasive and requires constant pacing, thus eliminating the role of memory (i.e. the dependence of a QT interval on preceding TQ and QT intervals). It is therefore clear that a robust methodology, which can detect instability of the QT interval directly from the clinical ECG and without invasive pacing is currently lacking. If such a methodology is developed, it could be used to predict an impending arrhythmia event from a patient clinical ECG or from an ICD electrogram recording.

SUMMARY

A method of predicting ventricular arrhythmias according to an embodiment of the current invention includes receiving an electrical signal from a subject's heart for a plurality of heart beats, identifying characteristic intervals and heart beat durations of the electrical signal corresponding to each of the plurality of heart beats to provide a plurality of characteristic intervals with corresponding heart beat durations, representing dynamics of the plurality of characteristic intervals as a function of a plurality of preceding characteristic intervals and durations of corresponding heart beats over a chosen period time, assessing a stability of the function over the chosen period of time, and predicting ventricular arrhythmias based on detected instabilities in the dynamics of the characteristic intervals.

A medical device according to an embodiment of the current invention has a system for predicting ventricular arrhythmias. The system has a data processor configured to receive an electrical signal from a subject's heart for a plurality of heart beats, identify characteristic intervals and heart beat durations of the electrical signal corresponding to each of the plurality of heart beats to provide a plurality of characteristic intervals with corresponding heart beat durations, represent the dynamics of the plurality of characteristic intervals as a function of a plurality of preceding characteristic intervals and durations of the corresponding heart beats over a chosen period of time, assess a stability of the function over the chosen period of time, and predict ventricular arrhythmias based on detected instabilities in the dynamics of the characteristic intervals.

A computer readable medium according to an embodiment of the current invention has stored executable instructions for execution by a computer. The executable instructions include executable instructions for receiving an electrical signal from a subject's heart for a plurality of heart beats, identifying characteristic intervals and heart beat durations of the electrical signal corresponding to each of the plurality of heart beats to provide a plurality of characteristic intervals with corresponding heart beat durations, representing dynamics of the plurality of characteristic intervals as a function of a plurality of preceding characteristic intervals and durations of corresponding heart beats over a chosen period time, assessing a stability of the function over the chosen period of time, and predicting ventricular arrhythmias based on detected instabilities in the dynamics of the characteristic intervals.

BRIEF DESCRIPTION OF THE DRAWINGS

Further objectives and advantages will become apparent from a consideration of the description, drawings, and examples.

FIG. 6A is an epicardial view of the image-based human ventricles model (ventricles in light, atria in dark). Atria were isolated from the ventricles during the simulation. ECG electrodes (E1 and E2) and pacing electrode (E3) are marked.

FIG. 6B is a transmural view of the model.

DETAILED DESCRIPTION

Figures 1A, 1B:
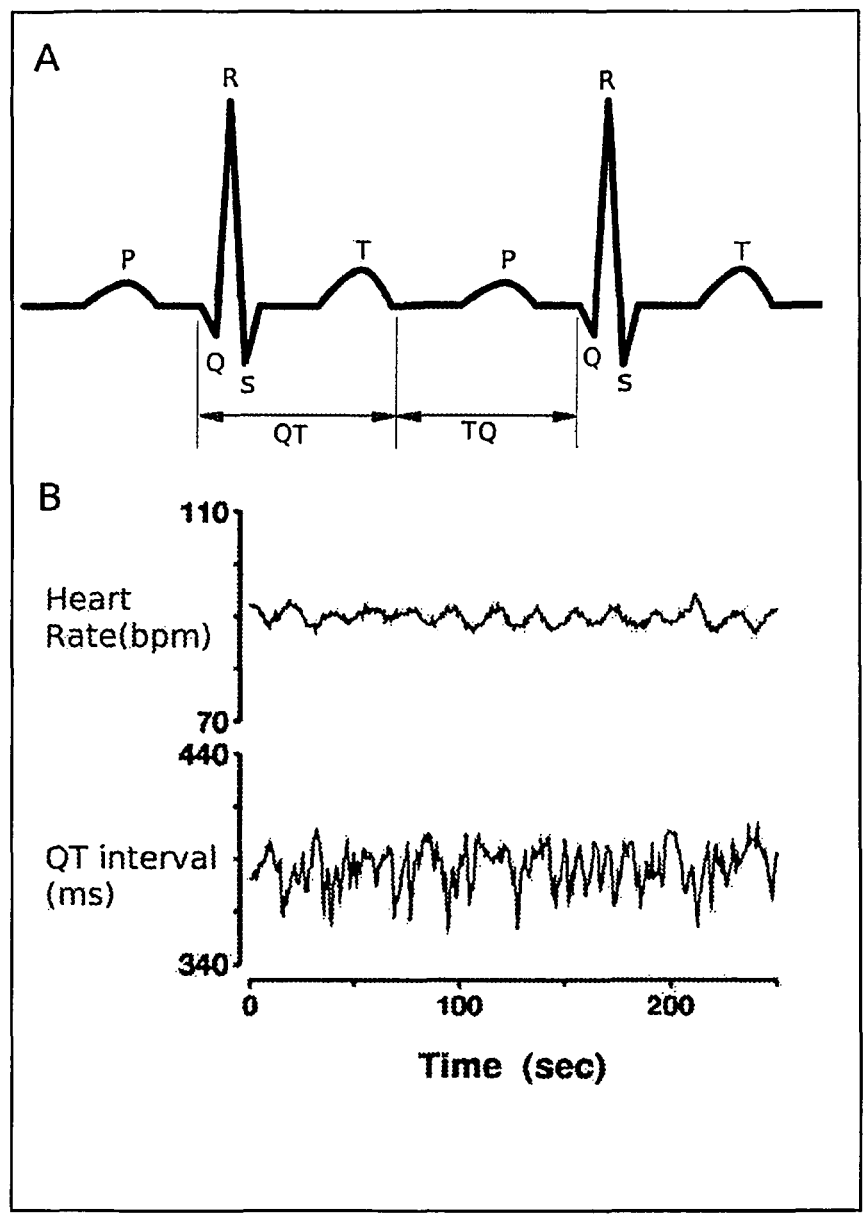
FIG. 1A shows an ECG trace with phases and intervals.
FIG. 1B shows an example of unstable QT dynamics recorded from a dilated cardiomyopathy patient.
Figure 2:
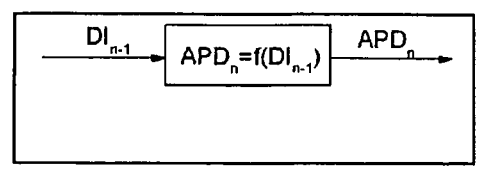
FIG. 2 a schematic illustration indicating that restitution is the dependence of APD on the preceding DI.
Figure 3:
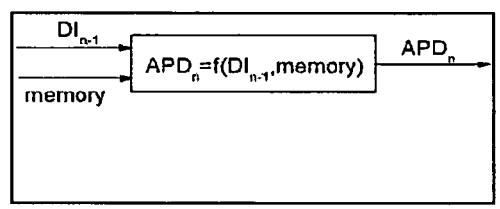
FIG. 3 is a schematic illustration of APD as a function of the preceding DI and memory. Here memory is an independent variable.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

In view of the above-summarized background, we considered the following question: Could the knowledge regarding the fact that APD instability is a function of both restitution and memory be translated to the clinic and used to detect patient QT interval instability and thus, his/her propensity to arrhythmia, directly from the clinical ECG and without invasive pacing? As mentioned above, the restitution concept has indeed been used to evaluate QT interval instability, however, such an approach is invasive and requires constant pacing, thus eliminating the role of memory The current approaches for assessing QT interval stability are statistical. Most notable among them is the QT variability index (QTVI) (Berger et al., supra; Murabayashi T, Fetics B, Kass D, Nevo E, Gramatikov B, Berger R D. Beat-to-beat QT interval variability associated with acute myocardial ischemia. J. Electrocardiol. 2002; 35(1):19-25; Vrtovec B, Starc V, Starc R. Beat-to-beat QT interval variability in coronary patients. J. Electrocardiol. 2000; 33(2):119-125). Such approaches evaluate the mean and standard deviation of the QT interval duration over the entire ECG, and thus provide an overall estimation of QT interval instability. However, they do not capture the development of QT interval instability from one beat to the next. Furthermore, ectopic beats are typically excluded from QTVI analysis, thus the approach focuses predominantly on the contribution of the autonomic nervous system (ANS) to QT interval stability. This contribution is, however, diminished in the diseased heart (Berger R D, Kasper E K, Baughman K L, Marban E, Calkins H, Tomaselli G F. Beat-to-beat QT interval variability: novel evidence for repolarization lability in ischemic and nonischemic dilated cardiomyopathy. Circulation. 1997; 96(5):1557-1565; Kleiger R, Miller J, Bigger J J, Moss A. Decreased heart rate variability and its association with increased mortality after acute myocardial infarction. *Am J. Cardiol.* 1987; 59(4): 256-262).

It is clear that a robust methodology, which can detect instability of the QT interval directly from the clinical ECG and without invasive pacing is currently lacking in the prior art. If such a methodology is developed, it could be used to predict an impending arrhythmia event from a patient clinical ECG or from an ICD electrogram. Some embodiments of the current invention can fill this void. Some embodiments of the current invention use, as a basis, the concepts and approaches to APD stability reviewed above. We then radically modify and extend these approaches to make them capable of assessing QT interval stability from clinical ECG recordings. All factors contributing to dynamic instability in QT interval, such as ANS influences as well as ectopic beats (the latter unmask QT interval instability in a manner much like small DIs unmask large APD restitution slopes) can be accounted for in embodiments of the current invention, rendering it a powerful tool in the assessment of propensity to arrhythmia from clinical ECG or ICD electrogram recordings. Although various embodiments of the current invention have utility in clinical practice, other embodiments of the current invention can also be used in basic science studies to evaluate APD stability.

Some embodiments of the current invention provide methods for detecting QT interval instability directly from clinical ECG or ICD electrogram recordings. Embodiments of the current invention provide a novel approach that is based on engineering methods never previously applied to cardiac electrophysiology. Application of this methodology in the clinic can provide methods and devices to monitor and detect QT interval instability and allow the clinician to assess the patient's propensity to arrhythmia, for example. Prediction of arrhythmia onset could provide a vital time window for early intervention and save human life. In the current environment which emphasizes reducing health care costs and optimizing therapy, robust diagnostic approaches to identify patients most susceptible to SCD would have a dramatic personal, medical and economic impact on the lives of many individuals.

Some aspects of the current invention provide a novel and radically different approach that overcomes the limitations of previous approaches that have failed to translate basic science concepts of restitution and cardiac memory into clinical applications. Systems and methods according to some embodiments of the current invention could be implemented in Holter monitors, treadmill stress tests, ICDs, and ECG-based devices, including those that monitor patients at locations remote from the hospital. Although some embodiments of the current invention are useful in clinical practice, some embodiments can be applied with equal ease in experiments and simulations, and at the level of the cell or tissue to assess local APD stability, and thus to facilitate the mechanistic inquiry into lethal ventricular arrhythmogenesis.

Figure 4:
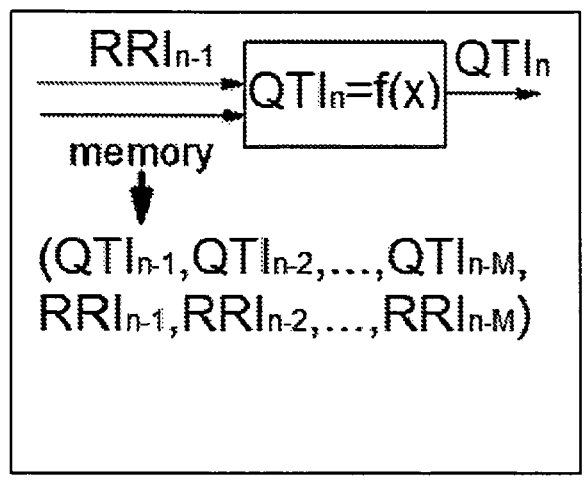
FIG. 4 is a schematic illustration of a system and method according to an embodiment of the current invention. In an embodiment, the QT interval (QTI) is a function of the preceding TQ interval (TQI), or equivalently of the preceding RR interval (RRI) since RRI=QTI+TQI, and memory. Memory is represented by the QTIs and RRIs (or TQIs) of M previous beats.

FIG. 4 is a schematic illustration to facilitate the description of a method and system for predicting ventricular arrhythmias according to an embodiment of the current invention. The method of predicting ventricular arrhythmias according to this embodiment of the current invention includes receiving an electrical signal from a subject's heart for a plurality of heart beats, identifying characteristic intervals and heart beat durations of the electrical signal corresponding to each of the plurality of heart beats to provide a plurality of characteristic intervals with corresponding heart beat durations, representing dynamics of the plurality of characteristic intervals as a function of a plurality of preceding characteristic intervals and durations of corresponding heart beats over a chosen period time (which can be as short as a single heart beat or longer), assessing the stability of this function (i.e. the stability of the dynamics of the characteristic intervals) over the chosen period of time, and predicting ventricular arrhythmias based on detected instabilities in the dynamics of the characteristic intervals over the said period of time. The electrical signal received can be an ECG or ICD electrogram signal, for example. However, other types of measurements of electrical activity of a subject's heart could also be used in other embodiments of the current invention. The characteristic interval can be a QT interval of an ECG or ICD electrogram signal according to some embodiments of the current invention.

The modeling of the plurality of characteristic intervals can include representing each QT interval as a function of a plurality of QT intervals and RR (or TQ) intervals. The modeling of the plurality of characteristic intervals can be done, but is not limited to, employing a linear autoregressive model with exogenous inputs (ARX) model, for example. The determining of the parameters of the QT interval dynamics model, according to an embodiment of the current invention based on the plurality of QT and RR (or TQ) intervals, can be done by determining the parameters $a_i$ and $b_i$ in the equation $$QTI_n = \sum_{i=1}^{M} a_i \times QTI_{n-i} + \sum_{i=1}^{M} b_i \times RRI_{n-i}$$

where QTI and RRI are QT and RR intervals, respectively; M is a number of heart beats included in the determining (this is memory); and n is a heart beat number.

The determining the instability in the dynamics of the characteristic intervals can include determining the instability of the ARX model above according to an embodiment of the current invention. The determining the instability of the ARX model can include taking a z-transform of the ARX model equation according to some embodiments of the current invention.

The method of predicting ventricular arrhythmias according to some embodiments of the current invention can also include evaluating the dependence of the instability in the dynamics of the characteristic intervals on the presence of premature heart beats. According to some embodiments, this can be done by counting the number of premature heart beats in the same periods of time over which instabilities in the dynamics of the characteristic intervals are evaluated. The method can further include calculating a ratio of the number of time periods with unstable dynamics in the ECG or ICD electrogram, divided by the number of time periods with premature heart beats, to provide a stratification index, such that predicting ventricular arrhythmias is based on the stratification index according to some embodiments of the current invention.

FIG. 4 schematically represents a medical device according to some embodiments of the current invention, which includes a system for predicting ventricular arrhythmias. The system includes a data processor configured to receive an electrical signal from a subject's heart for a plurality of heart beats, identifying characteristic intervals and heart beat durations of the electrical signal corresponding to each of the plurality of heart beats to provide a plurality of characteristic intervals with corresponding heart beat durations, representing dynamics of the plurality of characteristic intervals as a function of a plurality of preceding characteristic intervals and durations of corresponding heart beats over a chosen period time (which can be as short as a single heart beat or longer), assessing the stability of this function (i.e. the stability of the dynamics of the characteristic intervals) over the chosen period of time, and predicting ventricular arrhythmias based on detected instabilities in the dynamics of the characteristic intervals. The medical device can be, but is not limited to, a Holter monitor, a treadmill stress test device, an implantable cardioverter-defibrillators, or an ECG-based device, including devices that can monitor and/or respond in accordance with predictions of coronary arrhythmias according to an embodiment of the current invention.

Further embodiments of the current invention include a computer readable medium that/includes stored executable instructions for execution by a computer. The executable instructions include instructions for receiving an electrical signal from a subject's heart for a plurality of heart beats, identifying characteristic intervals and heart beat durations of the electrical signal corresponding to each of the plurality of heart beats to provide a plurality of characteristic intervals with corresponding heart beat durations, representing dynamics of the plurality of characteristic intervals as a function of a plurality of preceding characteristic intervals and durations of corresponding heart beats over a chosen period time (which can be as short as a single heart beat or longer), assessing the stability of this function (i.e. the stability of the dynamics of the characteristic intervals) over the chosen period of time, and predicting ventricular arrhythmias based on detected instabilities in the dynamics of the characteristic intervals.

Further embodiments of the current invention include computer programs configured to perform the methods of the current invention.

EXAMPLE 1

Instability in the dynamics of ventricular repolarization plays an important role in the mechanisms of arrhythmia, especially when a premature heart beat (i.e. premature activation, PA) is presented. At the cellular level, ventricular repolarization is measured by the action potential duration (APD), the latter often expressed as a function of the preceding diastolic interval (DI).[7] This relationship is known as APD restitution. Over the past decade, much emphasis has been placed on the restitution curve slope as a major factor in both the onset of arrhythmias, and the dynamic destabilization of reentrant waves that underlie arrhythmias. A large (>1) APD restitution slope indicates instability in APD dynamics;[7-9] it is observed in the short DI range, which is typically associated with PAs. The shorter the DI, the larger the restitution slope. Research has demonstrated that unstable APD dynamics results in spatial gradients in APD,[10-12] leads to ventricular tachycardia (VT) following PA,[1-3] and causes the transition from VT to ventricular fibrillation (VF).[8, 9, 12]

To test the importance of APD restitution slope as an arrhythmia risk index in the clinic, several studies have measured this slope in patients using monophasic action potential (MAP) catheters.[13, 14] These studies have reported increased APD restitution slopes in diseased human hearts, as identified by invasive constant-rate pacing protocols. The use of such pacing protocols eliminated short-term memory, which is the dependence of APD, in addition to the preceding DI, on activation history, typically represented by several previous APDs and DIs.[15, 16] Since short-term memory can either enhance or diminish the instability in APD dynamics,[17, 18] APD restitution slope cannot be used as an accurate measure of APD instability.

The QT interval (QTI) in an ECG is the global manifestation of ventricular APD. Based on the concept of APD restitution, larger-than-one slope of the QTI restitution (the dependence of QTI on the preceding TQ interval, TQI), which is an indicator of instability in QTI dynamics, has been tested as an index of arrhythmia risk.[17, 19, 20] However, similar to APD restitution slope, QTI restitution slope has to be measured under invasive constant-rate pacing protocols, which similarly eliminate the effect of short-term memory on QTI instability. Currently, there is no robust methodology that can detect instability in QTI non-invasively from the clinical ECG and without canceling the important contribution of short-term memory. Furthermore, it remains unknown whether instability in QTI dynamics, when detected, would be predictive of arrhythmia risk. Finally, the contributions of PA to instability in QTI dynamics and the onset of arrhythmias are also unknown. It these relationships are determined, a risk stratification index to predict the arrhythmia risk based on QTI instability can be developed.

In this example according to an embodiment of the current invention, we provide a novel methodology for detecting instability in QTI dynamics. The algorithm defines QTI as a function of both its preceding RR interval (RRI; RRI=QTI+TQI) and activation history (several preceding QTI and RRIs), and assesses the instability of this function. Because the effect of short-term memory is included in the algorithm, the resulting indicator of instability is more accurate than restitution slope. The methodology uses the clinical ECG and does not require a specific pacing protocol; it is thus noninvasive. In this example we test the hypotheses that instability in QTI dynamics, as detected by this methodology, precedes VT onset. Furthermore, we test the additional hypothesis that instability in QTI dynamics is positively correlated with the PA's degree of prematurity (DOP). The results of this example reveal the important contribution of PA and QTI instability to VT onset. Confirming these this hypotheses indicates that the present methodology according to some embodiments of the current invention for detecting instability in QTI dynamics could be used to develop an index that predicts risk of arrhythmias.

We tested the first hypothesis using clinical ECG recordings collected from acute myocardial infarction (AMI) patients. However, an ECG recording may have multiple PAs, each with different DOP, which makes directly testing the second hypothesis difficult. Instead, we used pseudo-ECG recordings generated using an MRI-based model of human ventricles, so that the DOP of PA can be controlled.

Methods

The details of the clinical data collection, the computer simulations, and the algorithm for detecting instability in QTI dynamics according to an embodiment of the current invention are presented in the following sections.

ECG Data

The ECG recordings used in this study were part of a clinical ECG database at the Johns Hopkins Hospital. All ECGs in the database were recorded with the specialized intensive care unit MARS telemetry system (GE Medical Systems, Milwaukee, Wis.). This system continuously records up to 28 hours of multi-lead ECG, sampled at 125 Hz.[21] From this database, 15 patients with either sustained (10) or non-sustained (5) monomorphic VT events were chosen. Among the 15 chosen patients, 7 (46.7%) were male, 2

(13.3%) were African American, and 13 (86.7%) were white. The mean average age was 67.2±3.9 years. All patients had coronary artery disease (CAD) and 6 (40%) patients used beta-blocker. From the multi-lead recordings of each patient, the recording with the best signal-to-noise ratio was chosen for analysis, thus avoiding additional filtering. VT events were identified from these ECG recordings by the cardiologist. Ten-minute-long ECG recordings, extracted immediately before VT onset and at least 1 hour before or after any arrhythmia event, were assembled into a VT and a control group, respectively, with one trace per patient in each group. Each 10-minute trace was then divided into ten 1-minute ECG recordings (minECGs).

Figure 5:
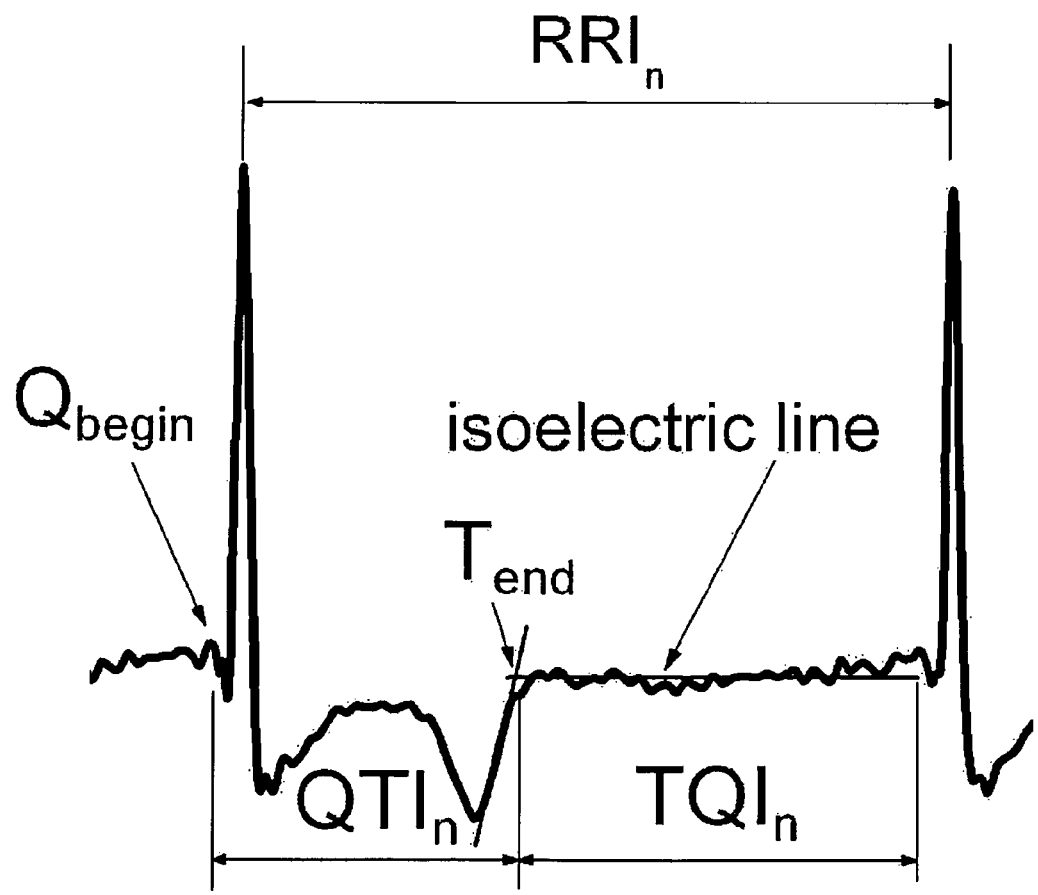
FIG. 5 illustrates ECG labeling used for an example according to the current invention.

For each minECG, Q, R, and T waves were labeled to extract QTI, TQI, and RRI. The QRS complex was first identified, followed by identification of the T wave and the isoelectric line using the approach of Laguna et al.[22] The end of the T wave was then found as the intersection of the isoelectric line with the tangent to the T wave at the point of maximum slope, as illustrated in FIG. 5. QTI, TQI, and RRI were defined as shown in FIG. 5. All labeling was visually checked to ensure accuracy. The number of PAs was also counted for each patient. Following the approach of Huikuri et al.,[23] a PA was counted when the RRI of the beat was shortened by at least 100 ms with respect to that of the preceding beat.

Computer Simulations

Figures 6, 6C:
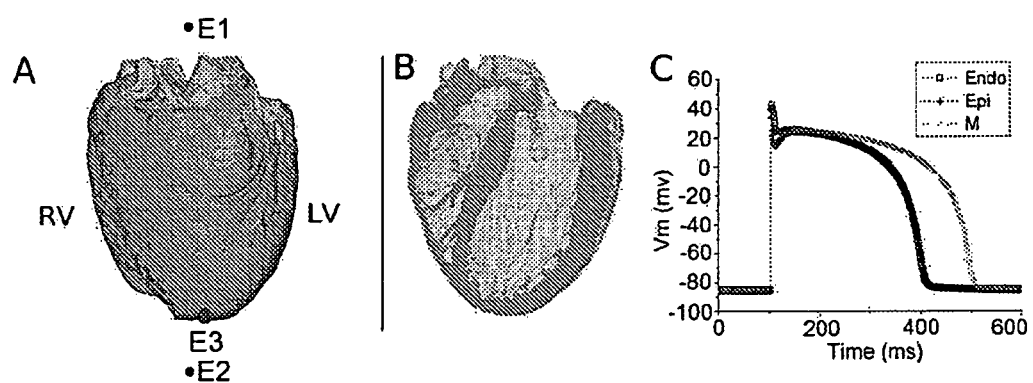
FIG. 6C shows action potential morphology of Endo-, M, and Epicardial cells.

We used the newly-developed anatomically realistic model of the human ventricles (FIG. 6A), reconstructed from MRI and diffusion-tensor (DT) MRI data,[24] to examine the effect of the DOP of PA on QTI instability. In this study, the DOP of a beat was defined as the shortening of the CI with respect to the one of the preceding beat.

Description of our pipeline for the model construction was published previously.[24, 25] Mathematical description of the electrical behavior of cardiac tissue was based on the monodomain representation, ensuring speed of execution of the simulations. The membrane dynamics of the human ventricular cell was represented by the ten Tuscher et al ionic model.[26] In order to obtain an ECG consistent with the clinical signal, we included transmural heterogeneities in cellular properties[26] in the model ventricles. The spatial distribution of endo-epi-, and M-cells across the ventricular walls (FIG. 6C) was implemented as in a previous study;[27] it was based on data by Drouin et al.[28]

Figure 6D:
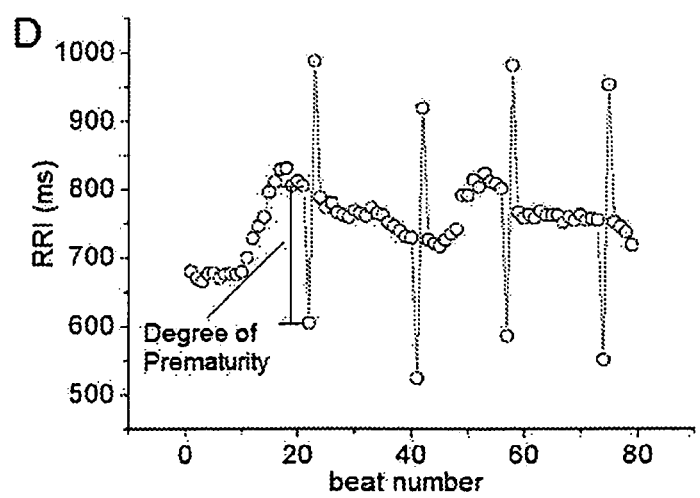
FIG. 6D shows RRI sequence with the artificially induced PAs. The DOP of PA was 0 ms, 150 ms, 200 ms, or 220 ms respectively at each pacing train.

A one-minute long pacing train was delivered epicardially at the apex of the human ventricular model (FIG. 6A). The pacing intervals in this train were the same as the RRIs of one of the PA-free minECGs in the control group. The timings of 4 randomly selected beats of this train were shortened to simulate PAs (FIG. 6D), with all 4 beats assumed to have the same DOP. This pacing protocol was implemented four times, with the same PA timings but different DOP values, namely 0 ms, 150 ms, 200 ms, and 220 ms. During each pacing protocol, one-minute long pseudo-ECGs (pseudo-minECGs) were computed as done previously.[27] The ECG leads were configured to record the Lead II of a standard 12-lead ECG system (FIG. 6A).

Assessment of Instability in QTI Dynamics

For each minECG or pseudo-minECG, the dependence of a given QTI on the preceding QTIs and RRIs was expressed as Equation 1, which is a linear autoregressive model with exogenous input (ARX). The latter has been used previously to describe APD dynamics.[16, 29]

$$QTI_n = \sum_{i=1}^{M} a_i \times QTI_{n-i} + \sum_{i=1}^{M} b_i \times RRI_{n-i} \quad \text{Equation 1}$$

In Equation 1, n is the beat number in the minECG or pseudo-minECG; $a_i$ and $b_i$ (i=1, ..., M) are the weights (constants) with which each preceding QTI and RRI, respectively, contributes to $QTI_n$. M is the number of beats representing the extent of the activation history.

The parameters of each ARX model were evaluated with an established approach termed Steiglitz-McBride iteration.[31] For each ARX model (i.e. each minECG or pseudo-minECG), the value of M was determined by increasing it from 1, in steps of 1, and examining, at each step, whether an accurate prediction of QTI dynamics in the minECG was achieved. The value of M at which the prediction reaches a predetermined accuracy is denoted as $K_{max}$. The predetermined accuracy in this study was that the mean square error between the predicted and the measured QTI was smaller than 5 $ms^2$.

We used a well-established method[32] to assess the stability of the ARX model (i.e. of Equation 1) and expressed it as a stability index, $P_m$. The definition and calculation of $P_m$ follows, below. Based on the value of $P_m$, the ARX model was found stable ($P_m<1$) or unstable ($P_m>=1$).[32] When the ARX model was unstable, the degree of instability was manifested in the value of $P_m$; the larger the value of $P_m$, the larger the instability.

To assess the stability of the ARX model, Equation 1 was rewritten as:

$$\sum_{i=0}^{M} a_i \times QT_{n-i} = \sum_{i=1}^{M} b_i \times RR_{n-i} \quad \text{Equation 2}$$

We applied a z-transform to Equation 2:

$$QT(z)(a_0+a_1z^{-1}+a_2z^{-2}+\ldots+a_Mz^{-M})=RR(z)(b_1z^{-1}+b_2z^{-2}+\ldots+b_Mz^{-M}). \quad \text{Equation 3}$$

and re-wrote the resulting equation as:

$$\frac{QT(z)}{RR(z)} = \frac{b_1z^{-1} + b_2z^{-2} + \ldots + b_Mz^{-M}}{a_0 + a_1z^{-1} + a_2z^{-2} + \ldots + a_Mz^{-M}} \quad \text{Equation 4}$$
$$= \frac{(z-\beta_1)(z-\beta_2)\ldots(z-\beta_M)}{(z-\alpha_1)(z-\alpha_2)\ldots(z-\alpha_M)}$$

Equation 4 is the transfer function of the ARX model expressed as Equation 1. Each $\alpha$ (or $\beta$) in Equation 4 is a complex number, and is called a pole (or a zero). The value of each pole (or zero) is determined by $a_i$ (or $b_i$) (i=0 to M), which are the weights determining the contribution of each QTI (or RRI). A pole can be cancelled by a zero if they are equal to each other. It can be proved that a system defined by Equation 4 is bounded-input bounded-output (BIBO) unstable if the magnitude of any un-cancelled pole is bigger than 1.[32] In this example, the maximum magnitude of all un-cancelled poles is termed as QTI instability index $P_m$. The z-transform operation and the calculation of pole and zero can be done with Matlab functions.

Data Analysis

Using the above algorithm, each minECG (or pseudo-minECG) was tagged as either stable or unstable based on its $P_m$ value. To test the 1st hypothesis, the number of unstable minECGs ($N_{us}$) was counted for each patient and was compared between the VT group and the control group using a paired t-test. The frequency of PA ($f_{PA}$) was also determined for each patient, and the relationship between $N_{us}$ and $f_{PA}$ was determined by calculating the correlation coefficient between these two variables for each group. We also compared $f_{PA}$ between the two groups with a paired t-test. The significance level of all these tests was 0.05. The second hypothesis was tested by comparing the $P_m$ indices of pseudo-minECGs with PAs of different DOP.

Results

ARX Modeling

Figure 7A:
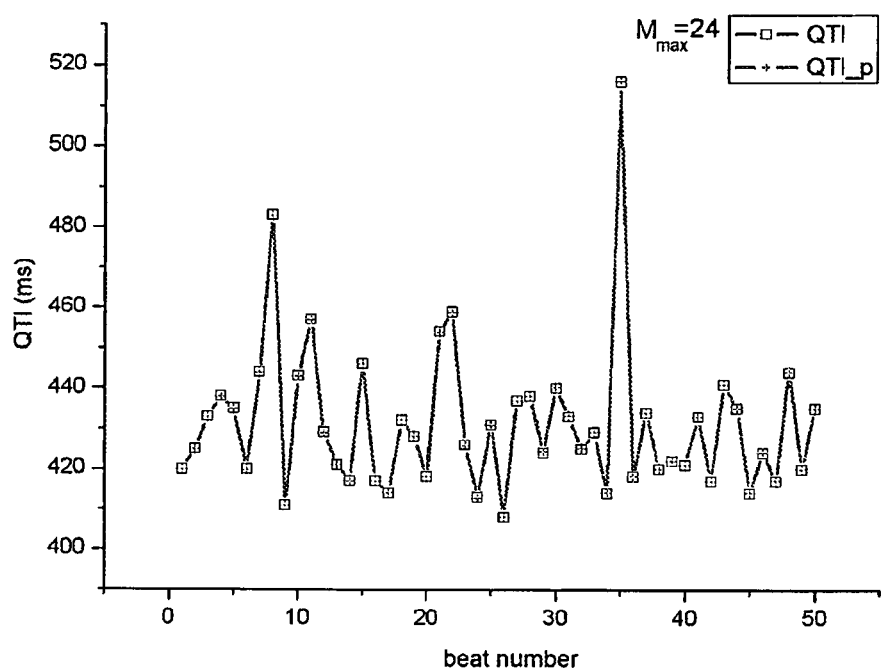
FIGS. 7A-7B show predicted QTI (QTI_p) dynamics of a minECG, compared with the same dynamics extracted directly from the patient ECG recording for $M_{max}$=24 (FIG. 7A) and M=3 (FIG. 7B).
Figure 7B:
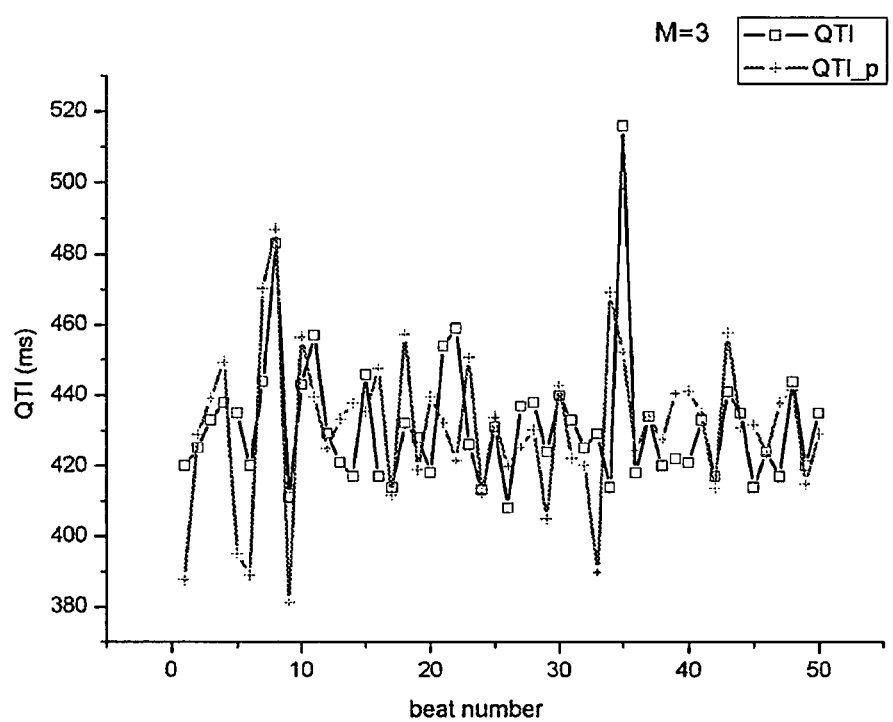
Figure 7C:
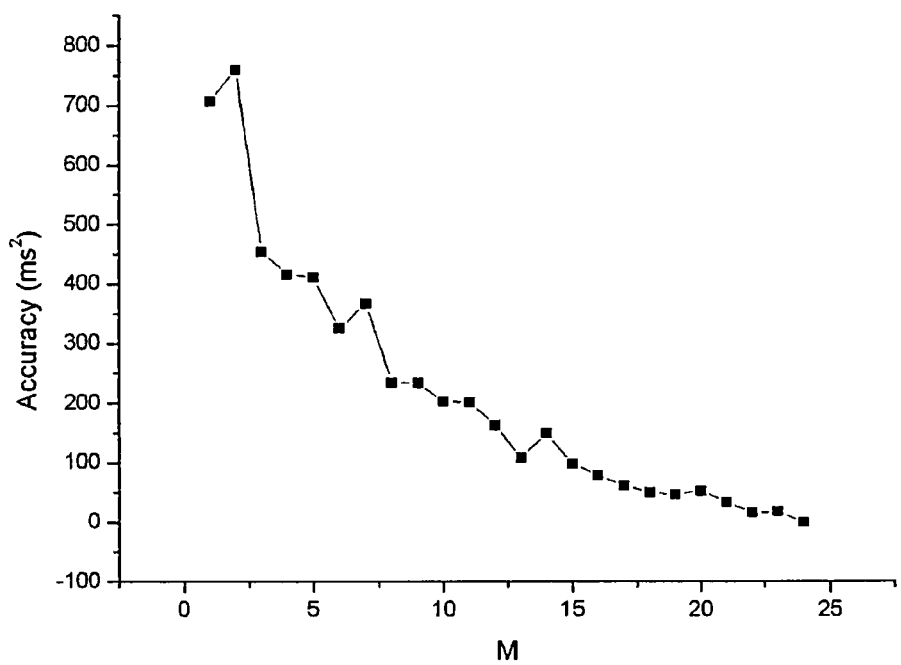
FIG. 7C shows the dependence of prediction accuracy on the value of M for the example of FIGS. 7A-7B.

An ARX model (Equation 1) was constructed for each minECG (or pseudo-minECG) and the value of each QTI in the minECG predicted. FIGS. 7A-7C show the predicted QTI dynamics for a single minECG, compared to the same dynamics extracted from the patient ECG recording. FIG. 7A demonstrates that an accurate prediction of QTI dynamics was achieved for $M_{max}$=24. FIG. 7B shows the predicted and the measured QTI dynamics for M=3. The dependence of QTI prediction accuracy on M is presented in FIG. 7C for the same minECG. The mean value of $M_{max}$ of the VT group was 37.8±8.8, which was significantly (p<0.00001) different from that of the control group (32.1±8.16).

QTI Instability in VT Group Vs. Control

Figure 8A:
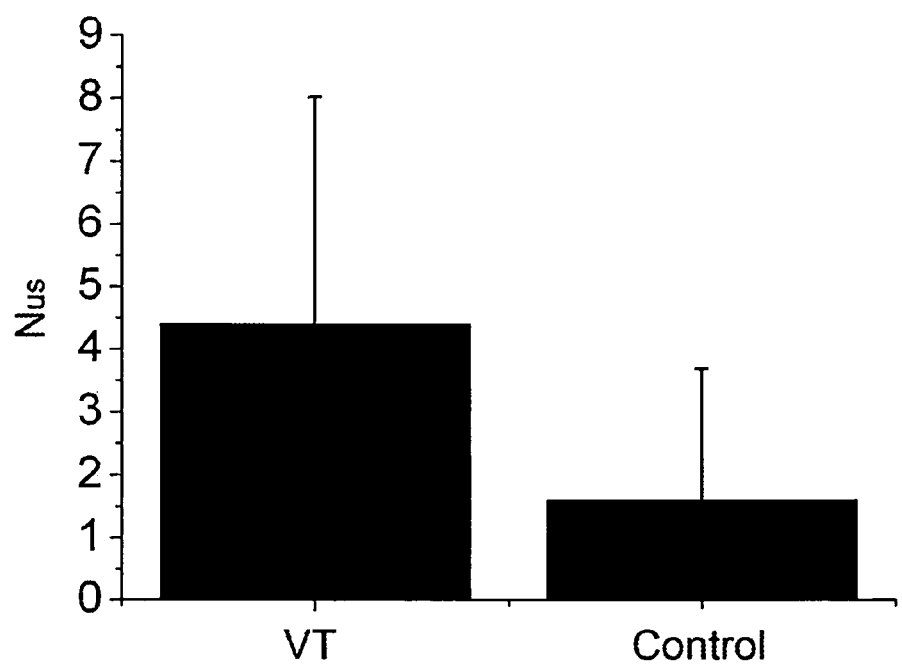
FIG. 8A shows a comparison of $N_{us}$ between the VT group and the control group.
Figure 8B:
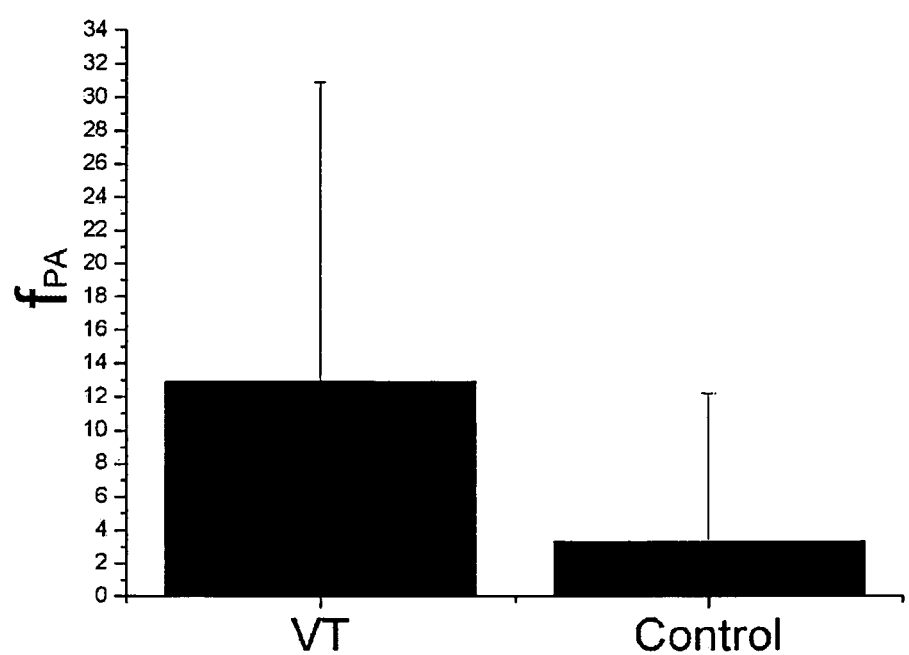
FIG. 8B shows a comparison of $f_{PA}$ between the VT group and the control group.

The value of $N_{us}$ was calculated for each patient in both groups, and is presented in Table 1. A paired t-test of the results in Table I showed that the mean $N_{us}$ value in the VT group (4.4±3.6) was significantly larger (p=0.003) than that in the control group (1.6±2.1) (FIG. 8A), which means that more minECGs became unstable before VT onset. We also found that the mean $f_{PA}$ of the VT group was higher, 12.9±17.96 beat/minute, than that of the control group, 3.3±8.9 beat/minute (p=0.029, FIG. 8B), indicating that the frequency of PAs increased before VT onset. Finally, we documented that $P_m$ values were always <1 in all PA-free minECGs, i.e., QTI dynamics in these minECGs was always stable. The correlation coefficient between $N_{us}$ and $f_{PA}$ was found to be 0.69 (p<0.05) in the VT group and 0.85 (p<0.01) in the control group.

TABLE 1

The number of unstable minECG in the VT group compared to those in the control group.

| Patient no. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| $N_{US}$ in VT group | 7 | 10 | 7 | 2 | 1 | 10 | 5 | 0 | 0 | 1 | 4 | 4 | 10 | 3 | 2 |
| $N_{US}$ in control group | 1 | 2 | 0 | 0 | 0 | 4 | 0 | 1 | 2 | 1 | 2 | 0 | 8 | 1 | 2 |

QTI Instability in Pseudo-minECGs with PAs of Different DOP

Under the PA-free pacing train (DOP of 0 ms), the QTI dynamics in the pseudo-minECG was stable (as it was in the original minECG from which the pacing train was extracted). For the modified pacing trains with non-zero DOP (DOP of 150 ms, 200 ms, and 220 ms), the values of $P_m$ of the corresponding pseudo-minECGs were 0.97, 1.001, and 1.02, respectively. Unstable QTI dynamics were thus observed for DOP of 200 ms and 220 ms. Clearly, increasing DOP revealed larger instability in QTI dynamics.

Discussion

This example presents an embodiment of a novel method for detecting instability in QTI dynamics from the ECG recording. By using this methodology, we were able to assess the contribution of unstable QTI dynamics to VT onset, and to explore the relationship between PA and QTI instability. The results of this study revealed increased frequency of PA and QTI instability before VT onset, and established that QTI instability is positively correlated with the DOP of PA. These findings shed light on the mechanisms of arrhythmogenesis, and indicate a possibility for the development of an index that predicts risk of arrhythmias from the clinical ECG.

This study revealed important contribution of PA and QTI instability to the onset of VT. It has been reported that unstable APD dynamics following PA is responsible for the VT onset. Researchers have hypothesized that unstable APD dynamics, caused by PA and large (>1) APD restitution slope, could lead to heterogeneous distribution of DI, and consequentially to the induction of conduction block, reentry, and VT.[1-3] However, this hypothesis has not been confirmed in the clinic. The measurement of APD restitution slope requires constant pacing protocols to eliminate short-term memory, while in the clinical setting, heart rhythm before arrhythmia onset is typically non-constant, and the contribution of short-term memory to QTI instability cannot be ignored. There is currently no reliable way to assess QTI instability from clinical recordings since short-term memory is present. The present study filled this void with a novel methodology that assesses QTI instability, with short-term memory being included. Applying this methodology to clinical ECG recorded from AMI patients, we identified unstable QTI dynamics before VT onset.

The contribution of PA and QTI instability to VT onset, as discussed in the above sections, is based on the assessment of QTI instability. In this study we represented QTI dynamics as an ARX model, an approach that has been used previously to determine the contribution of restitution and short-term memory to the value of APD.[16, 29] An ARX model (Equation 1) is composed of an autoregressive part (the $$\sum_{i=1}^{M} a_i \times QTI_{n-i}$$

part of Equation 1) and an exogenous part (the $$\sum_{i=1}^{M} b_i \times RRI_{n-i}$$

part of Equation 1). A novel aspect of the present methodology is the instability analysis of the ARX model.

Previous restitution research has reported that the restitution slope depends on the value of the preceding DI (or TQI). That is, restitution slope increases when DI (or TQI) decreases, and large (>1) restitution slope was only observed for small DI (or TQI) ranges. Performing the instability analysis of the ARX model, we observed a similar relationship between the DOP of PA and QTI instability. We found that unstable QTI dynamics was only observed when PA was presented, and the increased DOP of PA increased the instability of QTI dynamics.

Figure 9:
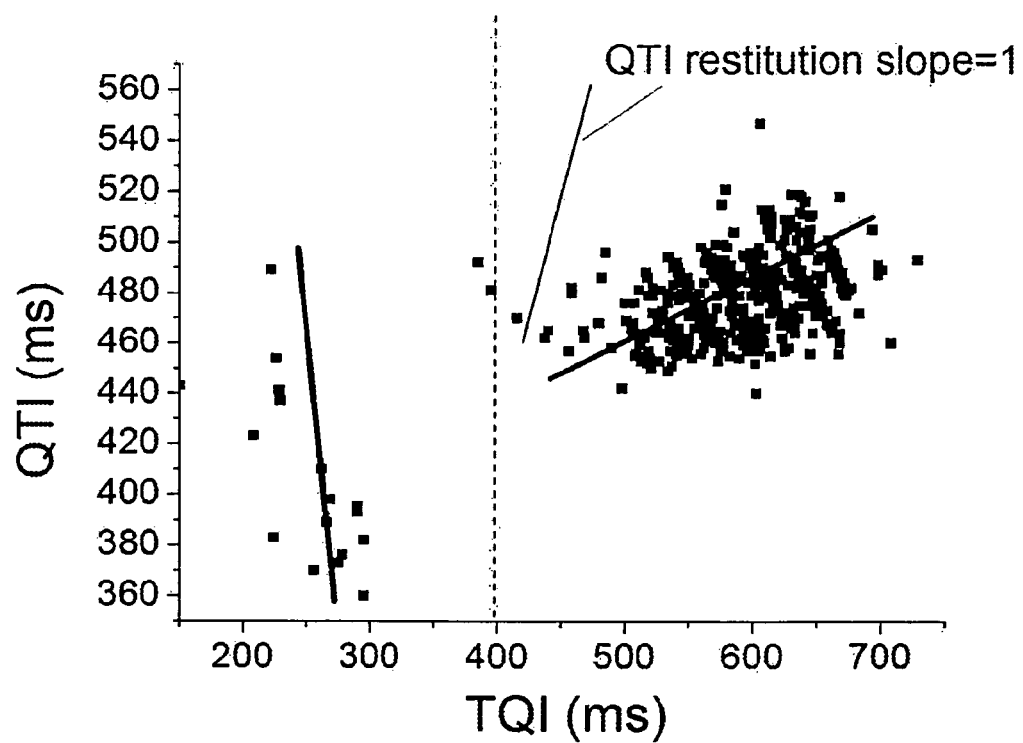
FIG. 9 shows the QTI restitution constructed from a minECG before the onset of VT according to an embodiment of the current invention. PA was presented in this minECG. Exponential QTI restitution curves were separately fitted in ranges TQI<=400 ms and TQI>400 ms.

The advantage of the present algorithm, compared against restitution, is that it is designed to accommodate short-term memory, while restitution is not. To demonstrate this advantage, a QTI restitution curve was constructed from QTI and TQI values of one minECG of the VT group (FIG. 9). PAs were presented in this minECG, and unstable QTI dynamics was identified with the present methodology. From FIG. 9, we can see that the QTI restitutions in the small TQI range (TQI<=400 ms) and the large TQI range (TQI>400 ms) are very different, and cannot be properly fitted with a single restitution curve. Instead, we fitted two exponential curves in these two ranges. In the small TQI range, the QTI restitution slope was negative; in the large TQI range, the slope is smaller than 1. Both slopes indicate stable QTI dynamics. Note that the curve fit presented in FIG. 9 was not possible for many other minECGs because large scatter in QTI restitution data points, indicative of strong short-term memory, exists in those minECGs.

Clinical Significance

The results of this study can be applied in both clinical monitoring for arrhythmia events and arrhythmia risk stratification. An important finding of the present study is that both $f_{PA}$ and $N_{US}$ increased before VT onset. We also found that QTI dynamics instability was dependent on the DOP of PA. These findings open a new way to predict the initiation of VT by monitoring $f_{PA}$, the DOP of PA, and $N_{US}$ in clinical ECG. We also want to emphasize that, because all the patients enrolled in this study had CAD, the positive correlation between $f_{PA}$ and $N_{US}$ reported for this example may not apply to the healthy heart. If this is proven to be the case, a positive correlation between $f_{PA}$ and $N_{US}$ in the ECG would indicate arrhythmic risk, and could be used as a risk stratification index.

The references cited for this example follow, in numerical order.

References

1. Gilmour R F, Gelzer A R, Otani N F. Cardiac electrical dynamics: maximizing dynamical heterogeneity. 2007; 40(6):S51-S55.
2. Fox J J, Riccio M L, Drury P, Werthman A, Gilmour R F. Dynamic mechanism for conduction block in heart tissue. *New Journal of Physics.* 2003; 5:101.101-101.104.
3. Otani N F. Theory of action potential wave block at-a-distance in the heart. *PHYSICAL REVIEW E.* 2007; 75:021910-021911-021910-021917.
4. Laurita K R, Girouard S D, Akar F G, Rosenbaum D S. Modulated Dispersion Explains Changes in Arrhythmia Vulnerability During Premature Stimulation of the Heart. *Circulation.* 1998; 98:2774-2780.
5. Laurita K R, Girouard S D, Rosenbaum D S. Modulation of ventricular repolarization by a premature stimulus. Role of epicardial dispersion of repolarization kinetics demonstrated by optical mapping of the intact guinea pig heart. *Circulation Research.* 1996; 79(3):493-503.
6. Narayan S M, Lindsay B D, Smith J M. Demonstration of the Proarrhythmic Preconditioning of Single Premature Extrastimuli by Use of the Magnitude, Phase, and Distribution of Repolarization Alternans. *Circulation.* 1999; 100:1887-1893.
7. Nolasco J B, Dahlen R W. A graphic method for the study of alternation in cardiac action potentials. *Journal Of Applied Physiology.* 1968; 25(2):191-196.
8. Koller M L, Riccio M L, Gilmour R F. Dynamic restitution of action potential duration during electrical alternans and ventricular fibrillation. *Am J Physiol.* 1998; 44:H1635-H1642.
9. Garfinkel A, Kim Y, Voroshilovsky O, Qu Z, Kil J, Lee M, Karagueuzian H, Weiss J, Chen P. Preventing ventricular fibrillation by flattening cardiac restitution. Proc Natl Acad Sci USA. 2000; 97:6061-6066.
10. Chen X, Fenton F H, Gray R A. Head-tail interactions in numerical simulations of reentry in a ring of cardiac tissue. *Heart Rhythm: The Official Journal Of The Heart Rhythm Society.* 2005; 2(9):1038-1046.
11. Watanabe M A, Fenton F H, Evans S J, Hastings H M, Karma A. Mechanisms for discordant alternans. *Journal Of Cardiovascular Electrophysiology.* 2001; 12(2):196-206.
12. Qu Z, Garfinkel A, Chen P S, Weiss J N. Mechanisms of discordant alternans and induction of reentry in simulated cardiac tissue. *Circulation.* 2000; 102(14):1664-1670.
13. Koller M L, Maier S K G, Gelzer A R, Bauer W R, Meesmann M, Robert F. Gilmour J. Altered Dynamics of Action Potential Restitution and Alternans in Humans With Structural Heart Disease. *Circulation.* 2005; 112: 1542-1548.
14. Selvaraj R J, Picton P, Nanthakumar K, Chauhan V S. Steeper restitution slopes across right ventricular endocardium in patients with cardiomyopathy at high risk of ventricular arrhythmias. *Am J Physiol Heart Circ Physiol* 2007; 292:H1262-H1268.
15. SHIFERAW Y, QU Z, GARFINKEL A, KARMA A, WEISS J N. Nonlinear Dynamics of Paced Cardiac Cells. *Annals of the New York Academy of Sciences.* 2006; 1080 (1):376-394.
16. Huang J, Zhou X, Smith W M, Ideker R E. Restitution properties during ventricular fibrillation in the in situ swine heart. *Circulation.* 2004; 110(20):3161-3167.
17. Gilmour R F, Otani N F, Watanabe M A. Memory and complex dynamics in cardiac Purkinje fibers. *American Journal of Physiology.* 1997; 272(4):H1826.
18. Otani N F, Gilmour R F. Memory Models for the Electrical Properties of Local Cardiac Systems. *J. Theor. Biol.* 1997; 187:409-436.
19. Yamauchi S, Yamaki M, Watanabe T, Yuuki K, Kubota I, Tomoike H. Restitution properties and occurrence of ventricular arrhythmia in LQT2 type of long QT syndrome. *Journal Of Cardiovascular Electrophysiology.* 2002; 13(9):910-914.
20. Fossa A A, Wisialowski T, Crimin K, Wolfgang E, Couderc J-P, Hinterseer M, Kaab S, Zareba W, Badilini F, Sarapa N. Analyses of Dynamic Beat-to-Beat QT-TQ Interval (ECG Restitution) Changes in Humans under Normal Sinus Rhythm and Prior to an Event of Torsades de Pointes during QT Prolongation Caused by Sotalol. *Annals Of Noninvasive Electrocardiology: The Official Journal Of The International Society For Holter And Noninvasive Electrocardiology, Inc.* 2007; 12(4):338-348.
21. Sachdev M, Fetics B J, Lai S, Dalai D, Inset J, Berger R D. Failure in Short-term Prediction of Ventricular Tachycardia and Ventricular Fibrillation from Continuous ECG in Intensive Care Unit Patients *J. Electrocardiology.* 2010; (in press).
22. Laguna P, Jane R, Caminal P. Automatic Detection of Wave Boundaries in Multilead ECG Signals: Validation with the CSE Database. *Computers and Biomedical Research.* 1994; 27(1):45-60.
23. Huikuri H V, Valkama J O, Airaksinen K E, Seppanen T, Kessler K M, Takkunen J T, Myerburg R J. Frequency domain measures of heart rate variability before the onset of nonsustained and sustained ventricular tachycardia in patients with coronary artery disease. *Circulation.* 1993; 87(4):1220-1228.
24. Vadakkumpadan F, Rantner L, Tice B, Boyle P, Prassl A, E. Vigmond, Plank G, Trayanova N. Image-based models of cardiac structure with applications in arrhythmia and defibrillation studies. *Journal of Electrocardiology.* 2009; 42(2):157.e151-157.e110.
25. Prassl A, Kickinger F, Ahammer H, Gran V, Schneider J, Hofer E, Vigmond E, Trayanova N, Plank G. Automatically Generated, Anatomically Accurate Meshes for Cardiac Electrophysiology Problems. *IEEE-TBME.* 2009; 56:1318-1330.
26. ten Tusscher K H, Noble D, Noble P J, Panfilov A V. A model for human ventricular tissue. *American Journal Of Physiology Heart And Circulatory Physiology.* 2004; 286 (4):H1573-1589.
27. Maharaj T, Blake R, Trayanova N, Gavaghan D, Rodriguez B. The role of transmural ventricular heterogeneities in cardiac vulnerability to electric shocks. *Progress In Biophysics And Molecular Biology.* 2008; 96(1-3):321-338.
28. Drouin E, Charpentier F, Gauthier C, Laurent K, Le Marec H. Electrophysiologic characteristics of cells spanning the left ventricular wall of human heart: evidence for presence of M cells. *J Am Coll Cardiol.* 1995; 26(1):185-192.
29. Toal S C, Farid T A, Selvaraj R, Chauhan V S, Masse S, Ivanov J, Harris L, Downar E, Franz M R, Nanthakumar K. Short-Term Memory and Restitution During Ventricular Fibrillation in Human Hearts An In Vivo Study *Circulation: Arrhythmia and Electrophysiology.* 2009; 2:562-570.
30. Nelles O. Nonlinear System Identification. *Springer-Verlag Berlin Heidelberg New York.* 2001:1.
31. Steiglitz K, McBRide L E. A Technique for the Identification of Linear Systems. *IEEE Trans. Automatic Control.* 1965; AC-10:461-464.
32. Lathi B P. LINEAR SYSTEMS AND SIGNALS. *Berkeley-Cambridge Press.* 1992:227.
33. Pastore J M, Girouard S D, Laurita K R, Akar F G, Rosenbaum D S. Mechanism linking T-wave alternans to the genesis of cardiac fibrillation. *Circulation.* 1999; 99(10):1385-1394.
34. Pruvot E J, Katra R P, Rosenbaum D S, Laurita K R. Role of Calcium Cycling Versus Restitution in the Mechanism of Repolarization Alternans. *Circulation Research.* 2004; 94:1083:1090.
35. Chinushi M, Restivo M, Caref E, El-Sherif N. Electrophysiological basis of arrhythmogenicity of QT/T alternans in the long QT syndrome: tridimensional analysis of the kinetics of cardiac repolarization. *Circ Res.* 1998; 83:614-628.
36. Rosenbaum D S, Jackson L E, Smith J M, Garan H, Ruskin J N, Cohen R J. Electrical Alternans and Vulnerability to Ventricular Arrhythmias. *N Engl J. Med.* 1994; 330:235-241.
37. Fox J J, McHarg J L, Gilmour R F. Ionic mechanism of electrical alternans. *Am J Physiol Heart Circ Physiol.* 2002; 282:H516-H530.

EXAMPLE 2

We have developed a novel algorithm to detect instability in QT interval (QTI) dynamics from clinical ECG recordings or ICD electrograms, as presented in Example 1. We demonstrated that QTI dynamics instability precedes the onset of ventricular tachycardia (VT) in patients with structural disease. We also demonstrated that the onset of VT is associated with increased frequency of premature activations (PA). In this example, using the developed algorithm to detect QTI dynamics instability, we constructed an arrhythmia risk stratification index. This index determines the dependence of QTI dynamics instability on the presence of PAs.

This example shows that the dependence of the instability in QTI dynamics on the presence of PA can be used to stratify arrhythmia risk in patients with structural heart disease.

The patient population had structural heart disease with an ICD implanted to provide an ICD recording, i.e., an EGM. The follow up of each patient terminated when the following endpoint events occurred:
1. The patient received appropriate ICD therapies (shock or pacing) when VT/VF was detected; or
2. Death.

For each patient, the risk stratification index needed assessment of the instability in QTI dynamics. The ECG or the electrogram trace from the ICD of each patient was divided into 1-minute long traces termed minECGs. The algorithm was applied to each minECG to detect whether QTI dynamics was unstable. The number of minECGs with unstable QTI dynamics was $N_{US}$. The number of minECGs with PAs present was $N_{PA}$.

The arrhythmia risk stratification index, termed QTI instability index (QTII), was defined as $$QTII = \frac{N_{us}}{N_{PA}}$$

Our rationale is to consider $N_{PA}$ as the perturbation of a system, and $N_{US}$ as the response of the system. QTII is the sensitivity of the system to the perturbation, that is, the sensitivity of $N_{US}$ to $N_{PA}$. QTII is this always less than 1.

To evaluate the prediction value of QTII, we used the following approaches:
1. Constructed Receiver Operating Characteristic (ROC) curve (sensitivity vs. 1-specificity for different QTII thresholds); and
2. Conducted Survival analysis (Kaplan-Meier and Cox).

Intracardiac electrocardiograms (EGMs) were recorded at rest in 44 patients with implanted ICDs. Patients were followed up for 29±16 months. During the follow up period, 11 patients received proper ICD therapies, and 8 patients died.

TABLE 2

| | Retrospective Analysis | | |
| --- | --- | --- | --- |
| | High Risk | Low Risk | P |
| Mean QTII | 0.91 ± 0.16 | 0.51 ± 0.35 | <0.0001 |
| Percentage of unstable minECGs (Nus/total number of minECGs) | 65 ± 33.7% | 32.2 ± 30.8% | <0.003 |

In the above table, the percentage of unstable minECGs was calculated over the total number of minECGs in each patient. From Table 2, one can see that the high-risk group (patients with endpoint events) has a larger QTII (significant) and more unstable minECGs (significant).

The sensitivity, specificity, relative risk (RR), and efficiency of the prediction for several example QTII values are listed in Table 3. The relationship between the sensitivity and specificity of the prediction for the QTII values used here is represented by the ROC curve (FIG. 10).

TABLE 3

| | Prospective Analysis | | | |
|---|---|---|---|---|
| QTII threshold | Sensitivity | Specificity | RR | Efficiency |
| >0.5 | 84.2% | 44% | 2.5 | 0.61 |
| >0.6 | 78.9% | 64% | 3.1 | 0.7 |
| >0.7 | 68.4% | 72% | 2.6 | 0.7 |
| =1 | 63.2% | 88% | 3.3 | 0.77 |

Figure 10:
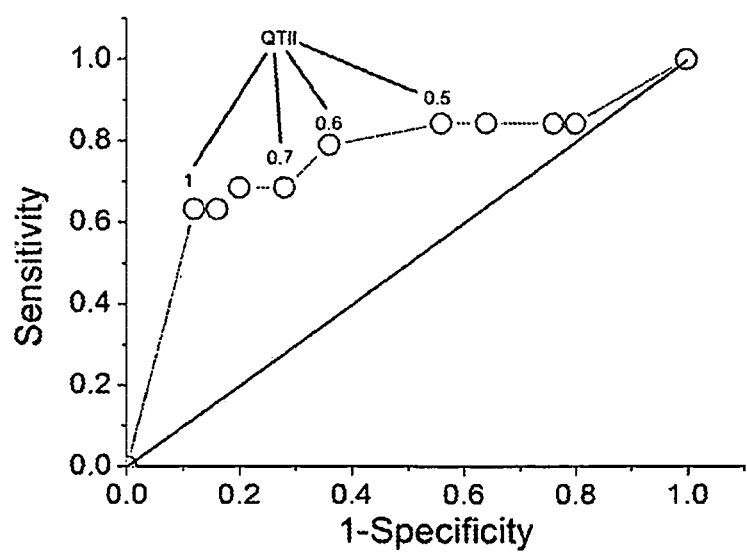
FIG. 10 shows the relationship between the sensitivity and 1-specificity of the prediction at different QTII values. The area under the curve indicates the accuracy of the prediction. The larger the area, the more accurate the prediction.
Figure 11:
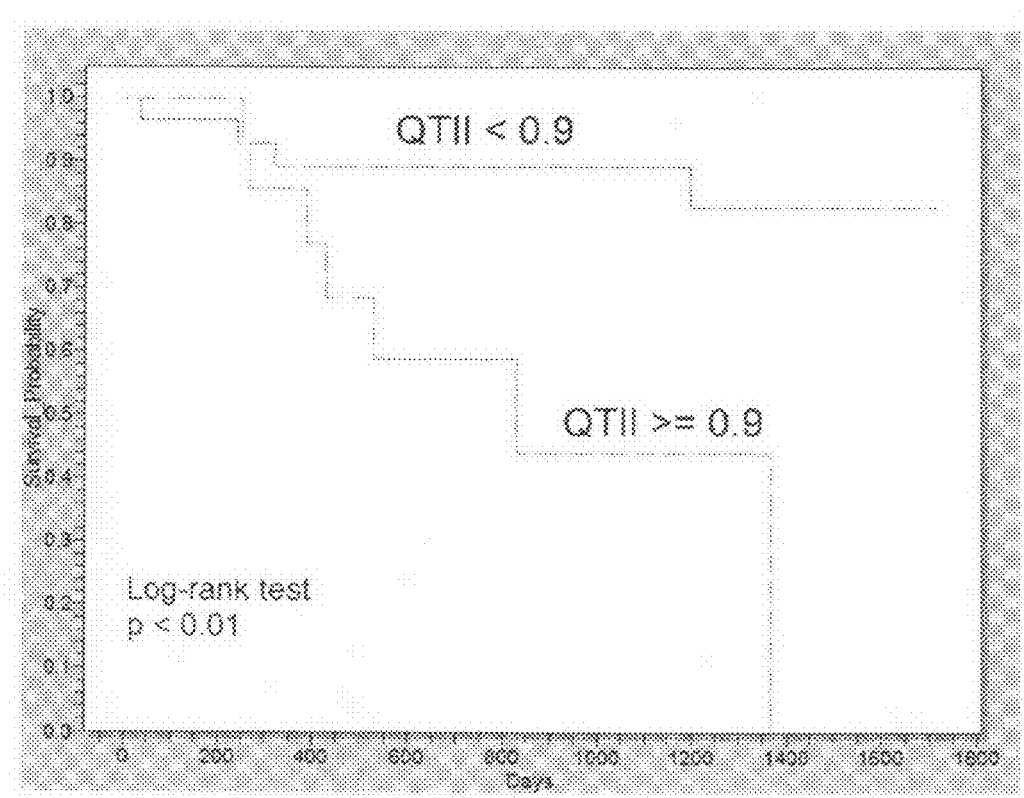
FIG. 11 shows the dynamics of survival probability in time for patients identified as being of either high risk (QTII=>0.9) or low risk (QTII<0.9) of arrhythmia. The difference between the two groups is statistically significant (p=0.001).

The area under the ROC curve was 0.76 (FIG. 10). For different QTII values (1>=QTII>=0.5), the relative risk ranges from 2.5 to 3.3; the hazard ratio (Cox survival analysis) ranges from 3.4 to 5.5 (p<0.05); the Log rank p value (Kaplan Meier test, FIG. 11) ranges from 0.0003 to 0.01. These results demonstrate that QTII can be used in the risk stratification of arrhythmia according to an embodiment of the current invention.

The embodiments illustrated and discussed in this specification are intended only to teach those skilled in the art the best way known to the inventors to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method of predicting ventricular arrhythmias, comprising:
   receiving an electrical signal from a subject's heart for a plurality of heart beats;
   identifying characteristic intervals and heart beat durations of the electrical signal corresponding to each of the plurality of heart beats to provide a plurality of characteristic intervals with corresponding heart beat durations;
   representing dynamics of said plurality of characteristic intervals as a function of a plurality of preceding characteristic intervals and durations of corresponding heart beats over a chosen period time;
   assessing a stability of said function over said chosen period of time; and
   predicting ventricular arrhythmias based on detected instabilities in the dynamics of said characteristic intervals,
   wherein said receiving an electrical signal is at least one of receiving an ECG or ICD electrogram signal,
   wherein said characteristic intervals are QT intervals of said at least one of said ECG or ICD electrogram signal,
   wherein said representing the dynamics of said plurality of characteristic intervals includes determining parameters of a QT interval dynamics model based on said QT intervals and on RR intervals, and
   wherein said QT interval dynamics model is an ARX model.

2. A method of predicting ventricular arrhythmias, comprising:
   receiving an electrical signal from a subject's heart for a plurality of heart beats;
   identifying characteristic intervals and heart beat durations of the electrical signal corresponding to each of the plurality of heart beats to provide a plurality of characteristic intervals with corresponding heart beat durations;
   representing dynamics of said plurality of characteristic intervals as a function of a plurality of preceding characteristic intervals and durations of corresponding heart beats over a chosen period time;
   assessing a stability of said function over said chosen period of time; and
   predicting ventricular arrhythmias based on detected instabilities in the dynamics of said characteristic intervals,
   wherein said receiving an electrical signal is at least one of receiving an ECG or ICD electrogram signal,
   wherein said characteristic intervals are QT intervals of said at least one of said ECG or ICD electrogram signal,
   wherein said representing the dynamics of said plurality of characteristic intervals includes determining parameters of a QT interval dynamics model based on said QT intervals and on RR intervals, and
   wherein said determining parameters of a QT interval dynamics model based on said QT intervals and RR intervals is determining parameters $a_i$ and $b_i$ in the following equation $$QTI_n = \sum_{i=1}^{M} a_i \times QTI_{n-i} + \sum_{i=1}^{M} b_i \times RRI_{n-i}$$

where M is a number of heart beats included in the determining and n is a heart beat number.

3. A method of predicting ventricular arrhythmias, comprising:
   receiving an electrical signal from a subject's heart for a plurality of heart beats;
   identifying characteristic intervals and heart beat durations of the electrical signal corresponding to each of the plurality of heart beats to provide a plurality of characteristic intervals with corresponding heart beat durations;
   representing dynamics of said plurality of characteristic intervals as a function of a plurality of preceding characteristic intervals and durations of corresponding heart beats over a chosen period time;
   assessing a stability of said function over said chosen period of time; and
   predicting ventricular arrhythmias based on detected instabilities in the dynamics of said characteristic intervals,
   wherein said receiving an electrical signal is at least one of receiving an ECG or ICD electrogram signal,
   wherein said characteristic intervals are QT intervals of said at least one of said ECG or ICD electrogram signal,
   wherein said representing the dynamics of said plurality of characteristic intervals includes determining parameters of a QT interval dynamics model based on said QT intervals and on RR intervals, and
   wherein said assessing the stability of said dynamics of said characteristic intervals comprises determining the stability of said model of said QT interval dynamics.

4. A method of predicting ventricular arrhythmias, comprising:
   receiving an electrical signal from a subject's heart for a plurality of heart beats;
   identifying characteristic intervals and heart beat durations of the electrical signal corresponding to each of the plurality of heart beats to provide a plurality of characteristic intervals with corresponding heart beat durations;

representing dynamics of said plurality of characteristic intervals as a function of a plurality of preceding characteristic intervals and durations of corresponding heart beats over a chosen period time;

assessing a stability of said function over said chosen period of time;

predicting ventricular arrhythmias based on detected instabilities in the dynamics of said characteristic intervals;

repeating said representing dynamics and said assessing a stability for a plurality of chosen periods of time; and counting a number of said plurality chosen periods of time in which an instability is detected to obtain a number represented as $N_{US}$.

5. A method of predicting ventricular arrhythmias according to claim 4, further comprising:

counting a number of said plurality chosen periods of time in which a premature heart beat occurs to obtain a number represented by $N_{PA}$;

calculating a ratio of $N_{US}$ divided by $N_{PA}$ to obtain a stratification index; and predicting ventricular arrhythmias based on said stratification index.

6. A method of predicting ventricular arrhythmias, comprising:

receiving an electrical signal from a subject's heart for a plurality of heart beats;

identifying characteristic intervals and heart beat durations of the electrical signal corresponding to each of the plurality of heart beats to provide a plurality of characteristic intervals with corresponding heart beat durations;

representing dynamics of said plurality of characteristic intervals as a function of a plurality of preceding characteristic intervals and durations of corresponding heart beats over a chosen period time;

assessing a stability of said function over said chosen period of time;

predicting ventricular arrhythmias based on detected instabilities in the dynamics of said characteristic intervals;

repeating said representing dynamics and said assessing a stability for a plurality of chosen periods of time; and counting a number of said plurality chosen periods of time in which an instability is detected to obtain a number represented as $N_{US}$, wherein said receiving an electrical signal is at least one of receiving an ECG or ICD electrogram signal, and wherein said characteristic intervals are QT intervals of said at least one of said ECG or ICD electrogram signal.

7. A method of predicting ventricular arrhythmias according to claim 6, further comprising:

counting a number of said plurality chosen periods of time in which a premature heart beat occurs to obtain a number represented by $N_{PA}$;

calculating a ratio of $N_{US}$ divided by $N_{PA}$ to obtain a stratification index; and predicting ventricular arrhythmias based on said stratification index.

8. A medical device comprising a system for predicting ventricular arrhythmias, said system comprising a data processor configured to:

receive an electrical signal from a subject's heart for a plurality of heart beats;

identify characteristic intervals and heart beat durations of the electrical signal corresponding to each of the plurality of heart beats to provide a plurality of characteristic intervals with corresponding heart beat durations;

represent the dynamics of said plurality of characteristic intervals as a function of a plurality of preceding characteristic intervals and durations of the corresponding heart beats over a chosen period of time;

assess a stability of said function over said chosen period of time; and predict ventricular arrhythmias based on detected instabilities in the dynamics of said characteristic intervals, wherein said electrical signal is at least one of an ECG or ICD electrogram signal, wherein said characteristic interval is a QT interval of said ECG or ICD electrogram signal, wherein said model of the dynamics of said plurality of characteristic intervals includes parameters determined for a QT interval model based on said plurality of QT and RR intervals, and wherein said model of the dynamics of said plurality of characteristic intervals is an ARX model.

9. A medical device comprising a system for predicting ventricular arrhythmias, said system comprising a data processor configured to:

receive an electrical signal from a subject's heart for a plurality of heart beats, identify characteristic intervals and heart beat durations of the electrical signal corresponding to each of the plurality of heart beats to provide a plurality of characteristic intervals with corresponding heart beat durations;

represent the dynamics of said plurality of characteristic intervals as a function of a plurality of preceding characteristic intervals and durations of the corresponding heart beats over a chosen period of time;

assess a stability of said function over said chosen period of time; and predict ventricular arrhythmias based on detected instabilities in the dynamics of said characteristic intervals, wherein said electrical signal is at least one of an ECG or ICD electrogram signal, wherein said characteristic interval is a QT interval of said ECG or ICD electrogram signal, wherein said model of the dynamics of said plurality of characteristic intervals includes parameters determined for a QT interval model based on said plurality of QT and RR intervals, and wherein said model of QT interval dynamics can be represented by the equation $$QTI_n = \sum_{i=1}^{M} a_i \times QTI_{n-i} + \sum_{i=1}^{M} b_i \times RRI_{n-i}$$

where M is a number of heart beats included in the determining parameters $a_i$ and $b_i$ and n is a heart beat number.

10. A medical device comprising a system for predicting ventricular arrhythmias, said system comprising a data processor configured to:

receive an electrical signal from a subject's heart for a plurality of heart beats;

identify characteristic intervals and heart beat durations of the electrical signal corresponding to each of the plurality of heart beats to provide a plurality of characteristic intervals with corresponding heart beat durations;

represent the dynamics of said plurality of characteristic intervals as a function of a plurality of preceding characteristic intervals and durations of the corresponding heart beats over a chosen period of time;

assess a stability of said function over said chosen period of time; and predict ventricular arrhythmias based on detected instabilities in the dynamics of said characteristic intervals, wherein said electrical signal is at least one of an ECG or ICD electrogram signal, wherein said characteristic interval is a QT interval of said ECG or ICD electrogram signal, wherein said model of the dynamics of said plurality of characteristic intervals includes parameters determined for a QT interval model based on said plurality of QT and RR intervals, and wherein said data processor is configured to determine stability of said dynamics of said characteristic intervals comprising determining the stability of said model of said QT interval dynamics.

11. A medical device comprising a system for predicting ventricular arrhythmias, said system comprising a data processor configured to:

receive an electrical signal from a subject's heart for a plurality of heart beats;

identify characteristic intervals and heart beat durations of the electrical signal corresponding to each of the plurality of heart beats to provide a plurality of characteristic intervals with corresponding heart beat durations;

represent the dynamics of said plurality of characteristic intervals as a function of a plurality of preceding characteristic intervals and durations of the corresponding heart beats over a chosen period of time;

assess a stability of said function over said chosen period of time;

predict ventricular arrhythmias based on detected instabilities in the dynamics of said characteristic intervals;

repeat said representing dynamics and said assessing a stability for a plurality of chosen periods of time; and count a number of said plurality chosen periods of time in which an instability is detected to obtain a number represented as $N_{US}$.

12. A medical device according to claim 11, wherein said data processor is further configured to count a number of said plurality chosen periods of time in which a premature heart beat occurs to obtain a number represented by $N_{PA}$;

calculate a ratio of $N_{US}$ divided by $N_{PA}$ to obtain a stratification index; and predict ventricular arrhythmias based on said stratification index.

13. A medical device comprising a system for predicting ventricular arrhythmias, said system comprising a data processor configured to:

receive an electrical signal from a subject's heart for a plurality of heart beats;

identify characteristic intervals and heart beat durations of the electrical signal corresponding to each of the plurality of heart beats to provide a plurality of characteristic intervals with corresponding heart beat durations;

represent the dynamics of said plurality of characteristic intervals as a function of a plurality of preceding characteristic intervals and durations of the corresponding heart beats over a chosen period of time;

assess a stability of said function over said chosen period of time;

predict ventricular arrhythmias based on detected instabilities in the dynamics of said characteristic intervals;

repeat said representing dynamics and said assessing a stability for a plurality of chosen periods of time; and count a number of said plurality chosen periods of time in which an instability is detected to obtain a number represented as $N_{US}$, wherein said electrical signal is at least one of an ECG or ICD electrogram signal, and wherein said characteristic interval is a QT interval of said ECG or ICD electrogram signal.

14. A medical device according to claim 13, wherein said data processor is further configured to:

count a number of said plurality chosen periods of time in which a premature heart beat occurs to obtain a number represented by $N_{PA}$;

calculate a ratio of $N_{US}$ divided by $N_{PA}$ to obtain a stratification index; and predict ventricular arrhythmias based on said stratification index.

15. A medical device comprising a system for predicting ventricular arrhythmias, said system comprising a data processor configured to:

receive an electrical signal from a subject's heart for a plurality of heart beats;

identify characteristic intervals and heart beat durations of the electrical signal corresponding to each of the plurality of heart beats to provide a plurality of characteristic intervals with corresponding heart beat durations;

represent the dynamics of said plurality of characteristic intervals as a function of a plurality of preceding characteristic intervals and durations of the corresponding heart beats over a chosen period of time;

assess a stability of said function over said chosen period of time; and predict ventricular arrhythmias based on detected instabilities in the dynamics of said characteristic intervals, wherein said medical device is at least one of a Holter monitor, a treadmill stress test device, an implantable cardioverter-defibrillator, or an ECG-based device.

16. A computer readable medium comprising stored executable instructions for execution by a computer, comprising executable instructions for:

receiving an electrical signal from a subject's heart for a plurality of heart beats;

identifying characteristic intervals and heart beat durations of the electrical signal corresponding to each of the plurality of heart beats to provide a plurality of characteristic intervals with corresponding heart beat durations;

representing dynamics of said plurality of characteristic intervals as a function of a plurality of preceding characteristic intervals and durations of corresponding heart beats over a chosen period time;

assessing a stability of said function over said chosen period of time; and predicting ventricular arrhythmias based on detected instabilities in the dynamics of said characteristic intervals, wherein said receiving an electrical signal is at least one of receiving an ECG or ICD electrigram signal, wherein said characteristic interval is a QT interval of said ECG or ICD electrogram signal, wherein said wherein said representing the dynamics of said plurality of characteristic intervals includes determining parameters of a QT interval dynamics model based on said QT intervals and on RR intervals, and wherein said wherein said QT interval dynamics model is an ARX model.

17. A computer readable medium comprising stored executable instructions for execution by a computer comprising executable instructions for:
  receiving an electrical signal from a subject's heart for a plurality of heart beats;
  identifying characteristic intervals and heart beat durations of the electrical signal corresponding to each of the plurality of heart beats to provide a plurality of characteristic intervals with corresponding heart beat durations;
  representing dynamics of said plurality of characteristic intervals as a function of a plurality of preceding characteristic intervals and durations of corresponding heart beats over a chosen period time;
  assessing a stability of said function over said chosen period of time; and
  predicting ventricular arrhythmias based on detected instabilities in the dynamics of said characteristic intervals,
  wherein said receiving an electrical signal is at least one of receiving an ECG or ICD electrigram signal,
  wherein said characteristic interval is a QT interval of said ECG or ICD electrogram signal,
  wherein said wherein said representing the dynamics of said plurality of characteristic intervals includes determining parameters of a QT interval dynamics model based on said QT intervals and on RR intervals, and
  wherein said determining parameters of a QT interval dynamics model based on said QT intervals and RR intervals is determining parameters $a_i$ and $b_i$ in the following equation $$QTI_n = \sum_{i=1}^{M} a_i \times QTI_{n-i} + \sum_{i=1}^{M} b_i \times RRI_{n-i}$$

where M is a number of heart beats included in the determining and n is a heart beat number.

18. A computer readable medium comprising stored executable instructions for execution by a computer, comprising executable instructions for:
  receiving an electrical signal from a subject's heart for a plurality of heart beats;
  identifying characteristic intervals and heart beat durations of the electrical signal corresponding to each of the plurality of heart beats to provide a plurality of characteristic intervals with corresponding heart beat durations;
  representing dynamics of said plurality of characteristic intervals as a function of a plurality of preceding characteristic intervals and durations of corresponding heart beats over a chosen period time;
  assessing a stability of said function over said chosen period of time; and
  predicting ventricular arrhythmias based on detected instabilities in the dynamics of said characteristic intervals,
  wherein said receiving an electrical signal is at least one of receiving an ECG or ICD electrigram signal,
  wherein said characteristic interval is a QT interval of said ECG or ICD electrogram signal,
  wherein said wherein said representing the dynamics of said plurality of characteristic intervals includes determining parameters of a QT interval dynamics model based on said QT intervals and on RR intervals, and
  wherein said assessing the stability of said dynamics of said characteristic intervals comprises determining the stability of said model of said QT interval dynamics.

19. A computer readable medium comprising stored executable instructions for execution by a computer, comprising executable instructions for:
  receiving an electrical signal from a subject's heart for a plurality of heart beats;
  identifying characteristic intervals and heart beat durations of the electrical signal corresponding to each of the plurality of heart beats to provide a plurality of characteristic intervals with corresponding heart beat durations;
  representing dynamics of said plurality of characteristic intervals as a function of a plurality of preceding characteristic intervals and durations of corresponding heart beats over a chosen period time;
  assessing a stability of said function over said chosen period of time; and
  predicting ventricular arrhythmias based on detected instabilities in the dynamics of said characteristic intervals,
  wherein said receiving an electrical signal is at least one of receiving an ECG or ICD electrigram signal,
  wherein said characteristic interval is a QT interval of said ECG or ICD electrogram signal,
  wherein said wherein said representing the dynamics of said plurality of characteristic intervals includes determining parameters of a QT interval dynamics model based on said QT intervals and on RR intervals, and
  wherein said determining the stability of said dynamics of said characteristic intervals comprises determining the stability of said model of said QT interval dynamics.

20. A computer readable medium comprising stored executable instructions for execution by a computer, comprising executable instructions for:
  receiving an electrical signal from a subject's heart for a plurality of heart beats;
  identifying characteristic intervals and heart beat durations of the electrical signal corresponding to each of the plurality of heart beats to provide a plurality of characteristic intervals with corresponding heart beat durations;
  representing dynamics of said plurality of characteristic intervals as a function of a plurality of preceding characteristic intervals and durations of corresponding heart beats over a chosen period time;
  assessing a stability of said function over said chosen period of time; and
  predicting ventricular arrhythmias based on detected instabilities in the dynamics of said characteristic intervals;
  repeating said representing dynamics and said assessing a stability for a plurality of chosen periods of time; and
  counting a number of said plurality chosen periods of time in which an instability is detected to obtain a number represented as $N_{US}$.

21. A computer readable medium according to claim 20, further comprising:
  counting a number of said plurality chosen periods of time in which a premature heart beat occurs to obtain a number represented by $N_{PA}$;
  calculate a ratio of $N_{US}$ divided by $N_{PA}$ to obtain a stratification index; and
  predicting ventricular arrhythmias based on said stratification index.

22. A computer readable medium comprising stored executable instructions for execution by a computer, comprising executable instructions for:
  receiving an electrical signal from a subject's heart for a plurality of heart beats;

identifying characteristic intervals and heart beat durations of the electrical signal corresponding to each of the plurality of heart beats to provide a plurality of characteristic intervals with corresponding heart beat durations;

representing dynamics of said plurality of characteristic intervals as a function of a plurality of preceding characteristic intervals and durations of corresponding heart beats over a chosen period time;

assessing a stability of said function over said chosen period of time;

predicting ventricular arrhythmias based on detected instabilities in the dynamics of said characteristic intervals;

repeating said representing dynamics and said assessing a stability for a plurality of chosen periods of time; and counting a number of said plurality chosen periods of time in which an instability is detected to obtain a number represented as $N_{US}$, wherein said receiving an electrical signal is at least one of receiving an ECG or ICD electrigram signal, wherein said characteristic interval is a QT interval of said ECG or ICD electrogram signal, and wherein said wherein said representing the dynamics of said plurality of characteristic intervals includes determining parameters of a QT interval dynamics model based on said QT intervals and on RR intervals.

23. A computer readable medium according to claim 22, further comprising:

counting a number of said plurality chosen periods of time in which a premature heart beat occurs to obtain a number represented by $N_{PA}$;

calculate a ratio of $N_{US}$ divided by $N_{PA}$ to obtain a stratification index; and predicting ventricular arrhythmias based on said stratification index.

* * * * *